(12) United States Patent
Fielding et al.

(10) Patent No.: US 8,696,710 B2
(45) Date of Patent: Apr. 15, 2014

(54) DEVICE AND ACCESSORIES FOR LIMITING FLEXION

(75) Inventors: Louis Fielding, San Carlos, CA (US); Anand Parikh, San Francisco, CA (US); Eller Torres, IV, Tracy, CA (US); Ian Bennett, San Francisco, CA (US); Hugues Malandain, Mountain View, CA (US); Jeffrey Schwardt, Palo Alto, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 67 days.

(21) Appl. No.: 13/267,394

(22) Filed: Oct. 6, 2011

(65) Prior Publication Data

US 2012/0265249 A1 Oct. 18, 2012

Related U.S. Application Data

(60) Provisional application No. 61/390,459, filed on Oct. 6, 2010.

(51) Int. Cl.
*A61B 17/70* (2006.01)

(52) U.S. Cl.
USPC ................... 606/263; 606/86 A; 606/246

(58) Field of Classification Search
USPC ......... 606/465, 249, 263, 151, 86 R, 74, 103, 606/246–248, 278–279, 86 A, 99, 105; 81/6, 10, 12, 173, 436, 473, 467, 476, 81/477

See application file for complete search history.

(56) References Cited

U.S. PATENT DOCUMENTS

| | | | | |
|---|---|---|---|---|
| 2,105,330 A | * | 1/1938 | Pagenkopf | 279/23.1 |
| 2,895,578 A | * | 7/1959 | Winchell | 192/41 S |
| 2,950,746 A | * | 8/1960 | Towne | 81/177.1 |
| 3,068,922 A | * | 12/1962 | Hill | 81/457 |
| 3,648,691 A | | 3/1972 | Lumb et al. | |
| 4,143,693 A | * | 3/1979 | Acevedo | 81/28 |
| 4,235,133 A | * | 11/1980 | Acevedo | 81/58 |
| 4,341,292 A | * | 7/1982 | Acevedo | 192/43 |
| 4,433,765 A | * | 2/1984 | Rude et al. | 192/41 S |
| 4,643,178 A | | 2/1987 | Nastari et al. | |
| 4,743,260 A | | 5/1988 | Burton | |
| 4,966,600 A | | 10/1990 | Songer et al. | |

(Continued)

FOREIGN PATENT DOCUMENTS

EP 0322334 A1 6/1989
FR 2681525 A1 3/1993

(Continued)

OTHER PUBLICATIONS

International search report and written opinion dated Apr. 2, 2012 for PCT/US2011/055136.

(Continued)

*Primary Examiner* — Ellen C Hammond
*Assistant Examiner* — Jacqueline Johanas
(74) *Attorney, Agent, or Firm* — Wilson Sonsini Goodrich & Rosati

(57) ABSTRACT

A device may be used to limit flexion of the spine without substantially limiting extension of the spine. Various accessories, instruments, and methods may be used to help deploy the flexion limiting device, manipulate, and adjust it.

27 Claims, 35 Drawing Sheets

(56) References Cited

U.S. PATENT DOCUMENTS

| | | | |
|---|---|---|---|
| 4,989,368 A * | 2/1991 | Trikilis | 49/42 |
| 5,011,494 A | 4/1991 | Von Recum et al. | |
| 5,092,866 A | 3/1992 | Breard et al. | |
| 5,116,340 A | 5/1992 | Songer et al. | |
| 5,139,093 A * | 8/1992 | Lyon et al. | 173/97 |
| 5,180,393 A | 1/1993 | Commarmond | |
| 5,282,863 A | 2/1994 | Burton | |
| 5,312,410 A * | 5/1994 | Miller et al. | 606/86 R |
| 5,325,950 A * | 7/1994 | Kimberlin | 192/41 S |
| 5,361,766 A | 11/1994 | Nichols et al. | |
| 5,395,374 A | 3/1995 | Miller et al. | |
| 5,415,658 A | 5/1995 | Kilpela et al. | |
| 5,415,661 A | 5/1995 | Holmes | |
| 5,431,075 A * | 7/1995 | Cruz et al. | 81/492 |
| 5,449,361 A * | 9/1995 | Preissman | 606/103 |
| 5,456,722 A | 10/1995 | McLeod et al. | |
| 5,462,542 A | 10/1995 | Alesi, Jr. | |
| 5,496,318 A | 3/1996 | Howland et al. | |
| 5,540,698 A | 7/1996 | Preissman | |
| 5,562,737 A | 10/1996 | Graf | |
| 5,609,634 A | 3/1997 | Voydeville | |
| 5,628,756 A | 5/1997 | Barker, Jr. et al. | |
| 5,645,599 A | 7/1997 | Samani | |
| 5,725,582 A | 3/1998 | Bevan et al. | |
| 5,902,305 A | 5/1999 | Beger et al. | |
| RE36,221 E | 6/1999 | Breard et al. | |
| 5,928,232 A | 7/1999 | Howland et al. | |
| 5,935,133 A | 8/1999 | Wagner et al. | |
| 5,964,769 A | 10/1999 | Wagner et al. | |
| 5,989,256 A | 11/1999 | Kuslich et al. | |
| 6,053,921 A | 4/2000 | Wagner et al. | |
| 6,203,545 B1 * | 3/2001 | Stoffella | 606/74 |
| 6,248,106 B1 | 6/2001 | Ferree | |
| 6,306,170 B2 | 10/2001 | Ray | |
| 6,312,431 B1 | 11/2001 | Asfora | |
| 6,364,883 B1 | 4/2002 | Santilli | |
| 6,378,289 B1 | 4/2002 | Trudeau et al. | |
| 6,391,030 B1 | 5/2002 | Wagner et al. | |
| 6,436,099 B1 | 8/2002 | Drewry et al. | |
| 6,451,019 B1 | 9/2002 | Zucherman et al. | |
| 6,468,309 B1 | 10/2002 | Lieberman | |
| 6,475,224 B1 * | 11/2002 | Pantages et al. | 606/159 |
| 6,556,857 B1 | 4/2003 | Estes et al. | |
| 6,582,433 B2 | 6/2003 | Yun | |
| 6,605,091 B1 | 8/2003 | Iwanski | |
| 6,626,944 B1 | 9/2003 | Taylor | |
| 6,629,975 B1 | 10/2003 | Kilpela et al. | |
| 6,652,527 B2 | 11/2003 | Zucherman et al. | |
| 6,652,585 B2 | 11/2003 | Lange | |
| 6,656,185 B2 | 12/2003 | Gleason et al. | |
| 6,669,729 B2 | 12/2003 | Chin | |
| 6,682,533 B1 | 1/2004 | Dinsdale et al. | |
| 6,689,140 B2 | 2/2004 | Cohen | |
| 6,689,168 B2 | 2/2004 | Lieberman | |
| 6,695,852 B2 | 2/2004 | Gleason | |
| 6,712,819 B2 | 3/2004 | Zucherman et al. | |
| 6,716,245 B2 | 4/2004 | Pasquet et al. | |
| 6,761,720 B1 * | 7/2004 | Senegas | 606/249 |
| 6,835,205 B2 | 12/2004 | Atkinson et al. | |
| 7,029,475 B2 | 4/2006 | Panjabi | |
| 7,080,719 B2 * | 7/2006 | Arnold et al. | 188/77 W |
| 7,163,558 B2 | 1/2007 | Senegas et al. | |
| 7,458,981 B2 * | 12/2008 | Fielding et al. | 606/279 |
| 7,584,734 B1 | 9/2009 | Fiorenza et al. | 123/179.31 |
| 8,096,998 B2 * | 1/2012 | Cresina | 606/103 |
| 8,257,367 B2 * | 9/2012 | Bryant et al. | 606/140 |
| 8,323,318 B2 * | 12/2012 | Baccelli et al. | 606/263 |
| 8,518,091 B2 * | 8/2013 | McDevitt et al. | 606/304 |
| 2002/0151978 A1 | 10/2002 | Zacouto et al. | |
| 2003/0078582 A1 | 4/2003 | Heggesness | |
| 2003/0083669 A1 * | 5/2003 | Gleason | 606/103 |
| 2004/0024458 A1 | 2/2004 | Senegas et al. | |
| 2004/0106995 A1 | 6/2004 | Le Couedic et al. | |
| 2004/0116927 A1 | 6/2004 | Graf | |
| 2004/0117017 A1 | 6/2004 | Pasquet et al. | |
| 2004/0127989 A1 | 7/2004 | Dooris et al. | |
| 2004/0138666 A1 | 7/2004 | Molz et al. | |
| 2004/0172132 A1 | 9/2004 | Ginn | |
| 2004/0243239 A1 | 12/2004 | Taylor | |
| 2005/0033435 A1 | 2/2005 | Belliard et al. | |
| 2005/0049708 A1 | 3/2005 | Atkinson et al. | |
| 2005/0192581 A1 | 9/2005 | Molz et al. | |
| 2005/0216017 A1 | 9/2005 | Fielding | |
| 2006/0069447 A1 | 3/2006 | Disilvestro et al. | |
| 2006/0136060 A1 | 6/2006 | Taylor | |
| 2006/0200134 A1 | 9/2006 | Freid et al. | |
| 2006/0240533 A1 | 10/2006 | Sengupta et al. | |
| 2007/0213829 A1 | 9/2007 | Le Couedic et al. | |
| 2007/0233096 A1 | 10/2007 | Garcia-Bengochea | |
| 2008/0009866 A1 | 1/2008 | Alamin et al. | |
| 2008/0082106 A1 | 4/2008 | Doll et al. | |
| 2008/0108993 A1 | 5/2008 | Bennett et al. | |
| 2008/0262549 A1 * | 10/2008 | Bennett et al. | 606/263 |
| 2008/0319487 A1 * | 12/2008 | Fielding et al. | 606/263 |
| 2009/0005817 A1 | 1/2009 | Friedrich et al. | |
| 2009/0018662 A1 * | 1/2009 | Pasquet et al. | 623/17.16 |
| 2009/0149960 A1 | 6/2009 | Hushka et al. | |
| 2009/0312801 A1 | 12/2009 | Lemoine et al. | |
| 2010/0023060 A1 | 1/2010 | Bennett et al. | |
| 2010/0106195 A1 | 4/2010 | Serhan et al. | |
| 2012/0059419 A1 * | 3/2012 | Alamin et al. | 606/263 |

FOREIGN PATENT DOCUMENTS

| | | |
|---|---|---|
| WO | WO 01/28442 A1 | 4/2001 |
| WO | WO 02/03882 A2 | 1/2002 |
| WO | WO 02/03882 A3 | 5/2002 |
| WO | WO 02/051326 A1 | 7/2002 |
| WO | WO 02/071960 A1 | 9/2002 |
| WO | WO 03/045262 A2 | 6/2003 |
| WO | WO 03/045262 A3 | 1/2004 |
| WO | WO 2004/052246 A1 | 6/2004 |
| WO | WO 2004/073532 A1 | 9/2004 |

OTHER PUBLICATIONS

Al Baz, et al. Modified technique of tension band wiring in flexion injuries of the middle and lower cervical spine. Spine (Phila Pa 1976). Jun. 1, 1995;20(11):1241-4.

Dickman, et al. Comparative mechanical properties of spinal cable and wire fixation systems. Spine (Phila Pa 1976). Mar. 15, 1997;22(6):596-604.

Garner, et al. Development and preclinical testing of a new tension-band device for the spine: the Loop system. Eur Spine J. Oct. 2002;11 Suppl 2:S186-91.

Heller, et al. Stability of different wiring techniques in segmental spinal instrumentation. An experimental study. Arch Orthop Trauma Surg. 1998;117(1-2):96-9.

Leahy, et al. Mechanical testing of a flexible fixation device for the lumbar spine. Proc Inst Mech Eng H. 2000;214(5):489-95.

Minns, et al. Preliminary design and experimental studies of a novel soft implant for correcting sagittal plane instability in the lumbar spine. Spine (Phila Pa 1976). Aug. 15, 1997;22(16):1819-25.

Miyasaka, et al. Radiographic analysis of lumbar motion in relation to lumbosacral stability. Investigation of moderate and maximum motion. Spine (Phila Pa 1976). Mar. 15, 2000;25(6):732-7.

Papp, et al. An in vitro study of the biomechanical effects of flexible stabilization on the lumbar spine. Spine (Phila Pa 1976). Jan. 15, 1997;22(2):151-5.

Shephard, et al. Slippage of a spinous process hook during flexion in a flexible fixation system for the lumbar spine. Med Eng Phys. Mar. 2001;23(2):135-41.

Shephard, et al. Spinous process strength. Spine (Phila Pa 1976). Feb. 1, 2000;25(3):319-23.

Voydeville, et al. Ligamentoplastie intervertebrate avec cale souple dans les instabilities lombaries. Intervertebral ligamentoplasty with flexible wedge in lumber instability. Orthop Traumatol. 1992;2:259-264.

\* cited by examiner

SECTION A-A

SECTION A-A

SECTION B-B

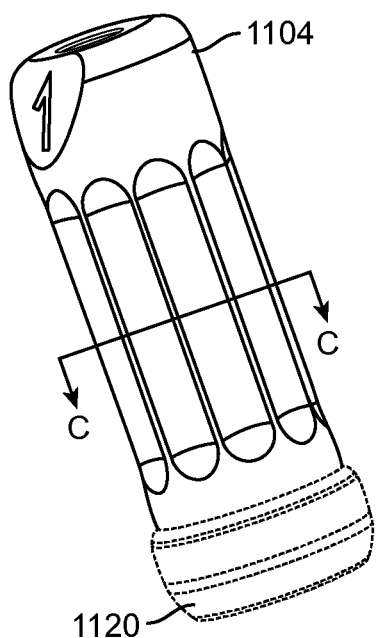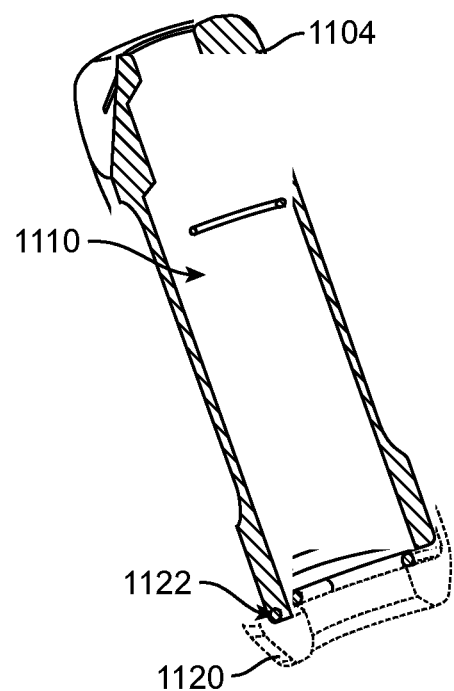
FIG. 11G
VIEW C-C
FIG. 11H

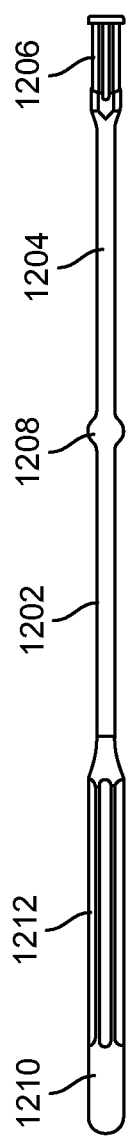
FIG. 12
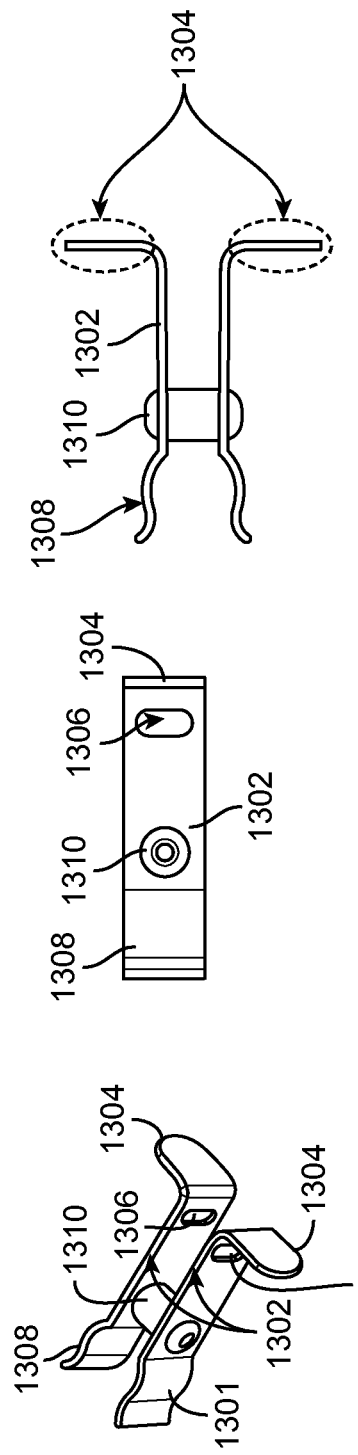
FIG. 13C
FIG. 13B
FIG. 13A

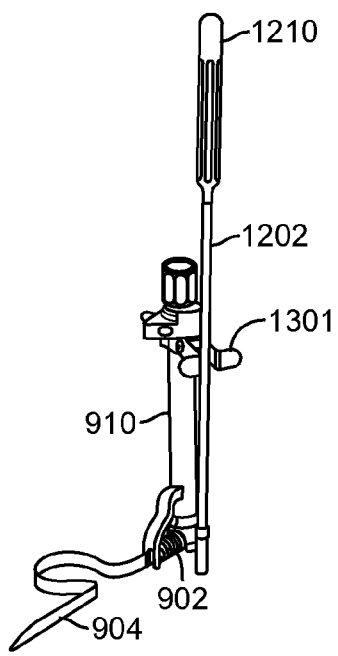
FIG. 14A
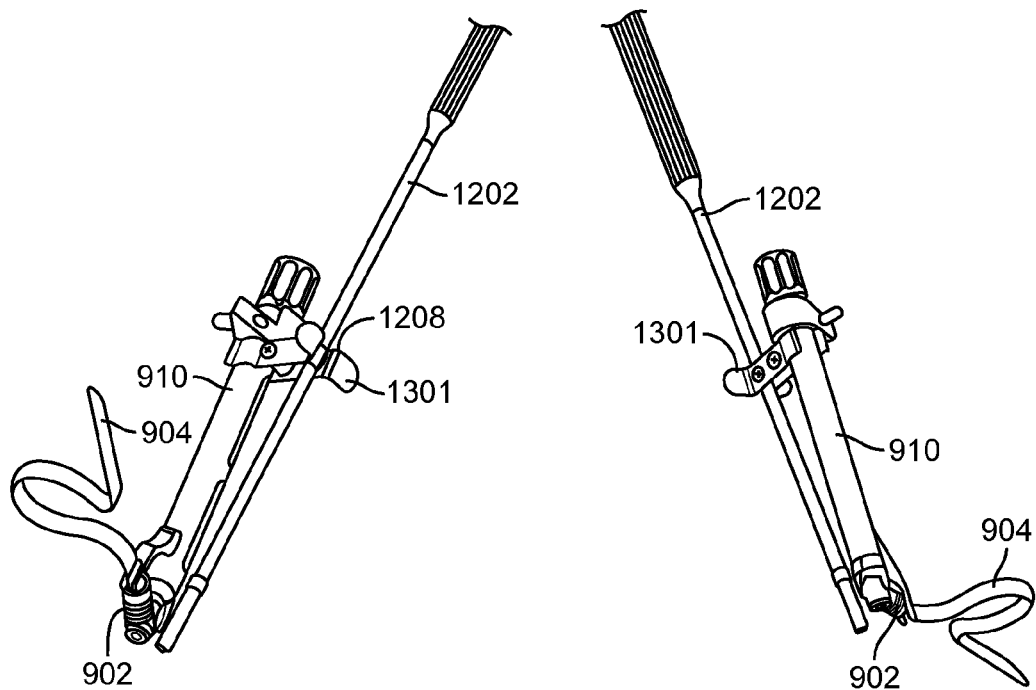
FIG. 14B
FIG. 14C

DEVICE AND ACCESSORIES FOR LIMITING FLEXION

CROSS-REFERENCE

The present application is a non-provisional of, and claims the benefit of U.S. Provisional Patent Application No. 61/390,459 filed Oct. 6, 2010, the entire contents of which are incorporated herein by reference.

This application is related to the following co-pending patent applications: Ser. Nos. 12/479,016 and 13/037,039; the entire contents of which are incorporated herein by reference.

BACKGROUND OF THE INVENTION

1. Field of the Invention

The present invention generally relates to medical methods and apparatus. More particularly, the present invention relates to orthopedic internal fixation such as methods, devices, and accessories for restricting spinal flexion in patients having back pain or for providing fracture fixation in long bone and trochanteric fractures or other orthopedic applications where a tether may be employed.

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine. Pain tends to be exacerbated when patients put their lumbar spines into flexion (i.e. by sitting or bending forward) and relieved when they put their lumbar spines into extension (i.e. by standing or arching backwards).

Flexion and extension are known to change the mechanical loading pattern of a lumbar segment. When the segment is in extension, the axial loads borne by the segment are shared by the disc and facet joints (approximately 30% of the load is borne by the facet joints). In flexion, the segmental load is borne almost entirely by the disc. Furthermore, the nucleus shifts posteriorly, changing the loads on the posterior portion of the annulus (which is innervated), likely causing its fibers to be subject to tension and shear forces. Segmental flexion, then, increases both the loads borne by the disc and causes them to be borne in a more painful way. Discogenic pain can be quite disabling, and for some patients, can dramatically affect their ability to work and otherwise enjoy their lives.

Pain experienced by patients with discogenic low back pain can be thought of as flexion instability, and is related to flexion instability manifested in other conditions. The most prevalent of these is spondylolisthesis, a spinal condition in which abnormal segmental translation is exacerbated by segmental flexion. The methods and devices described should as such also be useful for these other spinal disorders or treatments associated with segmental flexion, for which the prevention or control of spinal segmental flexion is desired. Another application for which the methods and devices described herein may be used is in conjunction with a spinal fusion, in order to restrict motion, promote healing, and relieve pain post-operatively. Alternatively, the methods and devices described should also be useful in conjunction with other treatments of the anterior column of the spine, including kyphoplasty, total disc replacement, nucleus augmentation and annular repair. General orthopedic or surgical applications are envisioned where a tether, cable or tape may be employed. An example is trochanteric fracture fixation in which a cerclage device is wrapped around the bone and is attached and tightened to facilitate fracture healing. Similarly, the device may also be used in conjunction with a cerclage device for the fixation of long bone fractures.

Patients with discogenic pain accommodate their syndrome by avoiding positions such as sitting, which cause their painful segment to go into flexion, and preferring positions such as standing, which maintain their painful segment in extension. One approach to reducing discogenic pain involves the use of a lumbar support pillow often seen in office chairs. Biomechanically, the attempted effect of the ubiquitous lumbar support pillow is also to maintain the painful lumbar segment in the less painful extension position.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebra. Fusion may or may not also include instrumentation of the affected spinal segment including, for example, pedicle screws and stabilization rods. Fusion is not usually recommended for discogenic pain because it is irreversible, costly, associated with high morbidity, and has questionable effectiveness. Despite its drawbacks, however, spinal fusion for discogenic pain remains common due to the lack of viable alternatives.

An alternative method, that is not commonly used in practice, but has been approved for use by the United States Food and Drug Administration (FDA), is the application of bone cerclage devices which can encircle the spinous processes or other vertebral elements and thereby create a restraint to motion. Physicians typically apply a tension or elongation to the devices that applies a constant and high force on the anatomy, thereby fixing the segment in one position and allowing effectively no motion. The lack of motion allowed after the application of such devices is thought useful to improve the likelihood of fusion performed concomitantly; if the fusion does not take, these devices will fail through breakage of the device or of the spinous process to which the device is attached. These devices are designed for static applications and are not designed to allow for dynamic elastic resistance to flexion across a range of motion. The purpose of bone cerclage devices and other techniques described above is to almost completely restrict measurable motion of the vertebral segment of interest. This loss of motion at a given segment gives rise to abnormal loading and motion at adjacent segments, which can lead eventually to adjacent segment morbidity.

Another solution involves the use of an elastic structure, such as tethers, coupled to the spinal segment. The elastic structure can relieve pain by increasing passive resistance to flexion while often allowing substantially unrestricted spinal extension. This mimics the mechanical effect of postural accommodations that patients already use to provide relief.

Spinal implants using tether structures are currently commercially available. One such implant couples adjacent vertebrae via their pedicles. This implant includes spacers, tethers and pedicle screws. To install the implant, selected portions of the disc and vertebrae bone are removed. Implants are then placed to couple two adjacent pedicles on each side of the spine. The pedicle screws secure the implants in place. The tether is clamped to the pedicle screws with set-screws, and limits the extension/flexion movements of the vertebrae of interest.

Because significant tissue is removed and because of screw placement into the pedicles, the implant and accompanying surgical methods are highly invasive and the implant is often irreversibly implanted. There is also an accompanying high chance of nerve root damage. Where the tip of the set-screw clamps the tethers, the tethers may be abraded and may generate particulate debris.

Other implants employing tether structures couple adjacent vertebrae via their processes instead. These implants include a tether and a spacer. To install the implant, the supraspinous ligament is temporarily lifted and displaced. The interspinous ligament between the two adjacent vertebrae of interest is then permanently removed and the spacer is inserted in the interspinous interspace. The tether is then wrapped around the processes of the two adjacent vertebrae, through adjacent interspinous ligaments, and then mechanically secured in place by the spacer or also by a separate component fastened to the spacer. The supraspinous ligament is then restored back to its original position. Such implants and accompanying surgical methods are not without disadvantages. These implants may subject the spinous processes to frequent, high loads during everyday activities, sometimes causing the spinous processes to break or erode. Furthermore, the spacer may put a patient into segmental kyphosis, potentially leading to long-term clinical problems associated with lack of sagittal balance. The process of securing the tethers is often a very complicated maneuver for a surgeon to perform, making the surgery much more invasive. And, as previously mentioned, the removal of the interspinous ligament is permanent. As such, the application of the device is not reversible.

More recently, less invasive spinal implants have been introduced. Like the aforementioned implant, these spinal implants are placed over one or more pairs of spinous processes and provide an elastic restraint to the spreading apart of the spinous processes during flexion. However, spacers are not used and interspinous ligaments are not permanently removed. As such, these implants are less invasive and may be reversibly implanted. The implants typically include a tether and a securing mechanism for the tether. The tether may be made from a flexible polymeric textile such as woven polyester (PET) or polyethylenes such as ultra high molecular weight polyethylene (UHMWPE); multi-strand cable, or another flexible structure. The tether is wrapped around the processes of adjacent vertebrae and then secured by the securing mechanism. The securing mechanism may involve the indexing of the tether and the strap, e.g., the tether and the securing mechanism include discrete interfaces such as teeth, hooks, loops, etc. which interlock the two. Highly forceful clamping may also be used to press and interlock the tether with the securing mechanism. Many known implementations can clamp a tether with the tip of a set-screw, or the threaded portion of a fastener.

The mechanical forces placed on the spinal implant are often unevenly distributed towards the specific portions of the tether and the securing mechanism which interface with each other. These portions are therefore typically more susceptible to abrasion, wear, or other damage, thereby potentially reducing the reliability of these spinal implants as a whole. Other known securing methods use a screw or bolt to draw other components together to generate a clamping force. While these methods may avoid the potentially damaging loads, the mechanical complexity of the assembly is increased by introducing more subcomponents. Other methods use a buckle through which the tether is threaded in a tortuous path, creating sufficient friction to retain the tether. These buckles generally distribute the load over a length of the tether; although they may be cumbersome to use and adjust as the tether is required to be threaded around multiple surfaces and through multiple apertures. Many of the aforementioned methods involve the use of several components, which must often be assembled during the surgical procedure, often within the wound. This adds time, complexity and risk to the surgical procedure. Additionally, several tools or instruments may be required to implant and adjust the device. These instruments or tools can be awkward or difficult to use and may require the surgeon and an assistant to hold the tools and manipulate them.

For the aforementioned reasons, it would be desirable to provide improved methods and apparatus to implant and secure the tethers of such spinal implants. In particular, such methods and apparatuses should be less invasive and should enable the tether to be more easily, reversibly, repeatably, safely and reliably secured to an implant by a surgeon, in a surgery setting. Such apparatuses should be ergonomically designed to so they are easy to manipulated and can accommodate various anatomies and physician positions. Additionally, the apparatuses should be easy to use with various features to ensure that tools are actuated in the proper direction when used. It would also be desirable if a single surgeon could operate all the tools without requiring an assistant. At least some of these objectives will be met by the embodiments disclosed herein.

2. Description of the Background Art

Patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; 5,928,232; 5,935,133; 5,964,769; 5,989,256; 6,053,921; 6,248,106; 6,312,431; 6,364,883; 6,378,289; 6,391,030; 6,468,309; 6,436,0909; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. US 2002/0151978; US 2004/0024458; US 2004/0106995; US 2004/0116927; US 2004/0117017; US 2004/0127989; US 2004/0172132; US 2004/0243239; US 2005/0033435; US 2005/0049708; 2005/0192581; 2005/0216017; US 2006/0069447; US 2006/0136060; US 2006/0240533; US 2007/0213829; US 2007/0233096; Published PCT Application Nos. WO 01/28442 A1; WO 02/03882 A2; WO 02/051326 A1; WO 02/071960 A1; WO 03/045262 A1; WO2004/052246 A1; WO 2004/073532 A1; and Published Foreign Application Nos. EP0322334 A1; and FR 2 681 525 A1. The mechanical properties of flexible constraints applied to spinal segments are described in Papp et al. (1997) Spine 22:151-155; Dickman et al. (1997) Spine 22:596-604; and Garner et al. (2002) Eur. Spine J. S186-S191; Al Baz et al. (1995) Spine 20, No. 11, 1241-1244; Heller, (1997) Arch. Orthopedic and Trauma Surgery, 117, No. 1-2:96-99; Leahy et al. (2000) Proc. Inst. Mech. Eng. Part H: J. Eng. Med. 214, No. 5: 489-495; Minns et al., (1997) Spine 22 No. 16:1819-1825; Miyasaka et al. (2000) Spine 25, No. 6: 732-737; Shepherd et al. (2000) Spine 25, No. 3: 319-323; Shepherd (2001) Medical Eng. Phys. 23, No. 2: 135-141; and Voydeville et al (1992) Orthop Traumatol 2:259-264.

SUMMARY OF THE INVENTION

The present invention provides fastening mechanisms, instruments, and methods for releasably locking an implantable surgical tether. Exemplary orthopaedic applications include restricting flexion of at least one spinal segment or securing broken bones together. More particularly, the provided fastening mechanisms, instruments, and methods relate to improvements to the methods and devices of deploying and implanting spinal implants for the treatment of discogenic pain and other conditions, such as degenerative spondylolisthesis. Specifically, such deployment and implantation methods are made less invasive, easier to operate, and more reliable and reversible by the provided fastening mechanisms and methods.

In a first aspect of the present invention, a system for adjusting tension in a surgical tether comprises an implantable surgical tether structure having a tether comprising a free end and a locking mechanism adapted to receive the tether. The locking mechanism is adapted to lock the free end of the tether in the locking mechanism when the tether is disposed therein such that the tether forms a loop that is adapted to encircle an anatomical structure. The locking mechanism is adapted to allow adjustment of loop size or tension therein. The system also includes a locking instrument operably coupled with the locking mechanism. Actuation of the locking instrument in a locking direction frictionally locks the tether in the locking mechanism thereby preventing slidable movement of the tether. The system also includes a tightening instrument and a braking component. The tightening instrument is adapted to receive the free end of the tether, and actuation of the tightening instrument in a tightening direction reduces the loop size or increases loop tension. Actuation of the tightening instrument in a loosening direction opposite the tightening direction increases the loop size or decreases loop tension. The braking component is coupled to the tightening instrument with sufficient friction to hold the tightening instrument in a tightened position after actuation of the tightening instrument in the tightening direction. The braking component is also coupled to the tightening instrument with sufficient friction to allow the tightening instrument to move from the tightened position to a loosened position when the locking instrument is actuated in the locking direction.

The surgical tether structure may comprise a superior loop segment and an inferior loop segment, and the superior loop segment may be adapted to be disposed around a superior spinous process, while the inferior loop segment may be adapted to be disposed around an inferior spinous process or sacrum. The surgical tether structure may comprise a first compliance member coupled with the locking mechanism, and the first compliance member may be adapted to provide a force resistant to flexion of a spinal segment. The surgical tether structure may further comprise a second compliance member that is disposed substantially parallel to the first compliance member. The first and the second compliance members may be adapted to be disposed on opposite sides of a spinal midline. The surgical tether structure may further comprise a second locking mechanism that is adapted to receive the tether. The second locking mechanism may be adapted to lock the tether in the second locking mechanism when the tether is disposed therein, and the second locking mechanism may be disposed substantially parallel to the other locking mechanism, each on opposite sides of a spinal midline.

The locking mechanism may comprise a roller rotatably disposed in a housing. The locking mechanism may comprise a slot passing therethrough, wherein the slot is sized to receive the tether. The locking mechanism slot may pass through the housing, and the roller may also comprise a through slot such that the slots are aligned with one another when the locking mechanism is unlocked. The slots may be misaligned with one another when the locking mechanism is locked. Rotation of the roller into a locked position may draw the tether into the housing from two directions. The locking mechanism may also include a stop mechanism having an engaged position and an unengaged position. In the engaged position the roller may be prevented from rotating, and in the disengaged position the roller may be free to rotate.

The locking instrument may comprise an elongate shaft which may be tubular and may have a distal end adapted to be releasably coupled with the locking mechanism. The locking instrument may comprise an inner shaft and an outer shaft. The inner shaft may be adapted to actuate the locking mechanism, and the outer shaft may be adapted to actuate a stop mechanism that prevents actuation of the locking mechanism into an unlocked position. Actuation of the locking mechanism in the locking direction may draw the tether into the locking mechanism from two directions.

The tightening instrument may comprise an elongate shaft releasably coupled with the tether. The tightening instrument may comprise a proximal end, a distal end, and a friction element disposed therebetween. The friction element may be adapted to allow the braking component to frictionally engage the tightening instrument. The friction element may comprise a spheroid or a ball. The tightening instrument may further comprise a handle coupled to a proximal end of the instrument.

The braking component may comprise a first arm coupled to a second arm. The first and second arms may be adapted to flex outward and biased to return to an inward position which may frictionally couple the braking component with the tightening instrument. A first end of the braking component may releasably engage the locking instrument, and a second end of the braking component opposite the first end may releasably engage the tightening instrument. The tightening instrument may comprise a friction element, and the first and second arms on the second end of the braking component each comprise an aperture for receiving the friction element.

In another aspect of the present invention, a method for adjusting tension in a surgical tether structure comprises providing an implantable surgical tether structure having a tether and a locking mechanism coupled thereto, inserting a portion of the tether into the locking mechanism, and tightening the tether structure by actuating a tightening instrument thereby pulling the tether through the locking mechanism. The method also includes maintaining tension in the tether structure with a braking component frictionally coupled to the tightening instrument, and locking the tether into the locking mechanism by actuating a locking instrument which draws the tether into the locking mechanism. The braking component permits retraction of the tether into the locking mechanism during actuation of the locking mechanism while maintaining tension in the tether structure.

The implantable surgical tether structure may comprise a first and second compliance member adapted to provide a force resistant to flexion of a spinal segment. The compliance members may be disposed on opposite sides of a spinal midline and they may be substantially parallel with one another. The surgical tether structure may resist flexion of the spinal segment substantially without restricting extension of the spinal segment. The surgical tether structure may comprise a superior loop segment and an inferior loop segment, and the method may further comprise disposing the superior loop segment around a superior spinous process, and disposing the inferior loop segment around an inferior spinous process or a sacrum.

Inserting a portion of the tether may comprise inserting a free end of the tether into the locking mechanism. Tightening the tether structure may comprise rotating the tightening instrument so that the tether rolls therearound. Tightening the tether structure may also comprise sliding the tether through a slot in the tightening instrument.

Maintaining tension may comprise engaging a pair of arms around the tightening instrument. The tightening instrument may comprise a friction element, and engaging the pair of arms may comprise disposing the arms around the friction element. Actuating the locking instrument may comprise rotating the locking instrument and/or rotating a roller in the locking mechanism. The method may also include engaging a stopping element with the locking mechanism to prevent actuation thereof.

In another aspect of the present invention, a system for indicating status in a surgical tether locking mechanism comprises an implantable surgical tether structure, a locking instrument, a stopping instrument, and an indicator plate. The implantable surgical tether structure has a tether and a locking mechanism adapted to receive the tether. The locking mechanism is adapted to lock the tether therein, and the locking mechanism also comprises a stopping element adapted to prevent over-actuation of the locking mechanism. The locking instrument is operably coupled with the locking mechanism such that actuation of the locking instrument in a locking direction actuates the locking mechanism into a locked position where the tether is frictionally locked in the locking mechanism. This prevents slidable movement of the tether. The stopping instrument is operably coupled with the stopping element. Actuation of the stopping instrument in an engaged direction actuates the stopping element into an engaged position which prevents actuation of the locking mechanism. The indicator plate is disposed adjacent the locking instrument and the stopping instrument. The indicator plate has indicia that indicates when the stopping element is in the engaged position or the disengaged position. The indicia also indicates when the locking mechanism is in the locked position or in the unlocked position, and the indicia indicates the direction to actuate the stopping instrument between the disengaged and the engaged positions, or the direction to actuate the locking mechanism between the unlocked and locked positions.

The system may further comprise a post extending from the indicator plate, and the post may be adapted to prevent over actuation of the stopping instrument beyond the engaged or disengaged position. The post may also be adapted to prevent over actuation of the locking instrument beyond the locked and unlocked position. The indicator plate may comprise a through hole sized to slidably receive the stopping instrument and the locking instrument. The through hole may be oblong in order to permit lateral movement of either the stopping instrument or the locking instrument when disposed therein. The indicator plate may comprise a second through hole that is sized to slidably receive a second stopping instrument and a second locking instrument. The indicator plate may comprise a figure eight shape, and the indicator plate may constrain lateral movement of the stopping instrument or the locking instrument.

In yet another aspect of the present invention, a method of adjusting tension and indicating status of a surgical tether comprises providing an implantable surgical tether structure having a tether and a locking mechanism, inserting the tether into the locking mechanism, and coupling a locking instrument with the locking mechanism. The locking mechanism also has a stopping element adapted to prevent over actuation of the locking mechanism. The method also comprises coupling a stopping instrument with the stopping element, and engaging an indicator plate with the locking instrument and the stopping instrument. The indicator plate has indicia that indicate a locked position and an unlocked position of the locking mechanism, and the indicia also indicate an engaged position and an unengaged position of the stopping element. In the locked position the tether is locked in the locking mechanism, and in the unlocked position the tether is movable through the slot. In the engaged position the locking mechanism is not actuatable, and in the unengaged (also referred to as disengaged) position the locking mechanism is actuatable. The method further comprises actuating the locking mechanism into either the locked or unlocked position by actuating the locking instrument until an indicia on the indicator plate indicates that the locking instrument is in the locked or unlocked position, and also actuating the stopping element into either the engaged or disengaged position by actuating the stopping instrument until an the indicia on the indicator plate indicates that the stopping instrument is in the engaged or disengaged position.

The indicator plate may comprise a through hole, and engaging the indicator plate may comprise sliding the locking instrument and the stopping instrument through the through hole. The locking mechanism may comprise a housing and a roller disposed therein with the housing having the slot passing therethrough and the roller having a slot passing therethrough. Actuating the locking mechanism may comprise rotating the roller so that the slots are either aligned or misaligned with one another. Actuating the locking instrument or the stopping instrument may comprise rotating an elongate shaft. Actuating the stopping element may comprise rotating the stopping element into engagement with the locking mechanism or rotating the stopping element to disengage from the locking mechanism. The method may further comprise preventing over actuation of the locking mechanism beyond the locked or unlocked position by constraining actuation of the locking instrument with a post coupled with the indicator plate. The method similarly may also include preventing over actuation of the stopping element beyond the engaged or disengaged position by constraining actuation of the stopping instrument with a post coupled with the indicator plate.

In another aspect of the present invention, an actuator mechanism for one-way actuation of a medical device comprises an ergonomically shaped handle designed to fit in a surgeon's hand, a coil spring disposed in the handle, and an elongate shaft at least partially disposed in a central channel of the spring which is coiled to form the central channel. One end of the spring is coupled with the handle. Rotation of the handle in a first direction reduces the spring central channel diameter so as to constrict around the elongate shaft so that handle rotation is transmitted to the elongate shaft causing rotation of the elongate shaft. Rotation of the handle in a second direction opposite the first direction increases the spring central channel diameter thereby releasing the elongate shaft from the torsion spring so that handle rotation is not transmitted to the elongate shaft resulting in no rotation thereof. An end of the spring may form a protuberance that is captured in an aperture of the handle. The torsion spring may comprise a welded region that joins the torsion spring with the handle.

In still another aspect of the present invention, a method for one-way actuation of a medical device comprises providing an actuating mechanism comprising an ergonomically shaped handle designed to fit in a surgeon's hand, a spring coupled to the handle and being coiled to form a central channel, and an elongate shaft disposed in the central channel. The method also includes rotating the handle in a first direction such that the central channel diameter reduces and constricts around the elongate shaft thereby transmitting rotation of the handle to rotation of the elongate shaft, and rotating the handle in a second direction opposite the first direction such that the central channel diameter increases so that the central shaft is disengaged therefrom thereby preventing transmission of handle rotation to the shaft.

Rotating the handle in the first direction may lock the surgical ether disposed on the locking mechanism.

In another aspect of the present invention, a system for adjusting tension in a surgical tether comprises an implantable surgical tether structure having a tether and a locking mechanism. The locking mechanism is adapted to lock the tether when the tether is disposed in the locking mechanism. The system also has a tether tightening instrument adapted to tighten the tether. The tether tightening instrument comprises a handle having one or more friction elements, a central channel, and a receiver, and an elongate shaft having a cross-pin and a slot near a distal end thereof sized to receive the tether. The handle slidably receives the elongate shaft in the central channel such that rotation of the handle is transmitted into rotation of the elongate shaft when the cross-pin is engaged with the receiver so that the tether is tightened. Also rotation of the elongate shaft is constrained due to friction between the elongate shaft and the one or more friction elements, but rotation of the elongate shaft is still permitted when sufficient counter torque is applied thereto. The constraint or rotation of the elongate shaft is provided when the handle slidably receives the elongate shaft in the central channel and the cross-pin remains disengaged from the receiver so that the tether remains at least partially tightened. The elongate shaft may further comprise a quick release knob for disengaging the elongate shaft from the handle. The one or more friction elements may comprise tabs on the elongate shaft or on the handle. The elongate shaft may have a longitudinal axis and the cross-pin may be transverse thereto. The slot may slidably receive the tether and the tether is spooled around the elongate shaft when the elongate shaft is rotated in a first direction, and wherein the tether is unspooled from the elongate shaft when the elongate shaft is rotated in a second direction opposite the first direction.

In another aspect of the present invention, a method for tightening a surgical strap comprises providing an implantable surgical tether structure having a tether and a locking mechanism with a slot therein. The locking mechanism is adapted to lock the tether when the tether is disposed in the slot. The method also includes frictionally engaging a handle with an elongate shaft. The handle has a central channel and a receiver and the elongate shaft has a cross-pin and a slot near a distal end of the elongate shaft, the elongate shaft slidably disposed in the central channel. The cross-pin is disposed in the receiver, and the handle is actuated thereby actuating the elongate shaft and tightening the tether. Disengaging the cross-pin from the receiver still maintains frictional engagement of the handle with the elongate shaft so as to prevent rotation of the elongate shaft and maintain tension in the tether until a counter torque sufficient to overcome the frictional engagement between the handle and the elongate shaft is applied thereto thereby allowing release of the tension in the tether.

Frictionally engaging the handle with the elongate shaft may comprise engaging one or more friction tabs on the handle with the elongate shaft. Actuating the handle may comprise rotating the handle in a first direction so that the tether spools around the elongate shaft. The counter torque may be applied when the locking mechanism is actuated to lock the tether therein.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 11A-11K illustrate embodiments of a one-way driver.

FIG. 12 illustrates an exemplary tightening instrument.

FIGS. 13A-13C illustrate an exemplary braking component.

FIGS. 14A-14C illustrate use of the braking component in FIGS. 13A-13C with the tightening instrument of FIG. 12.

DETAILED DESCRIPTION OF THE INVENTION

Figure 1:
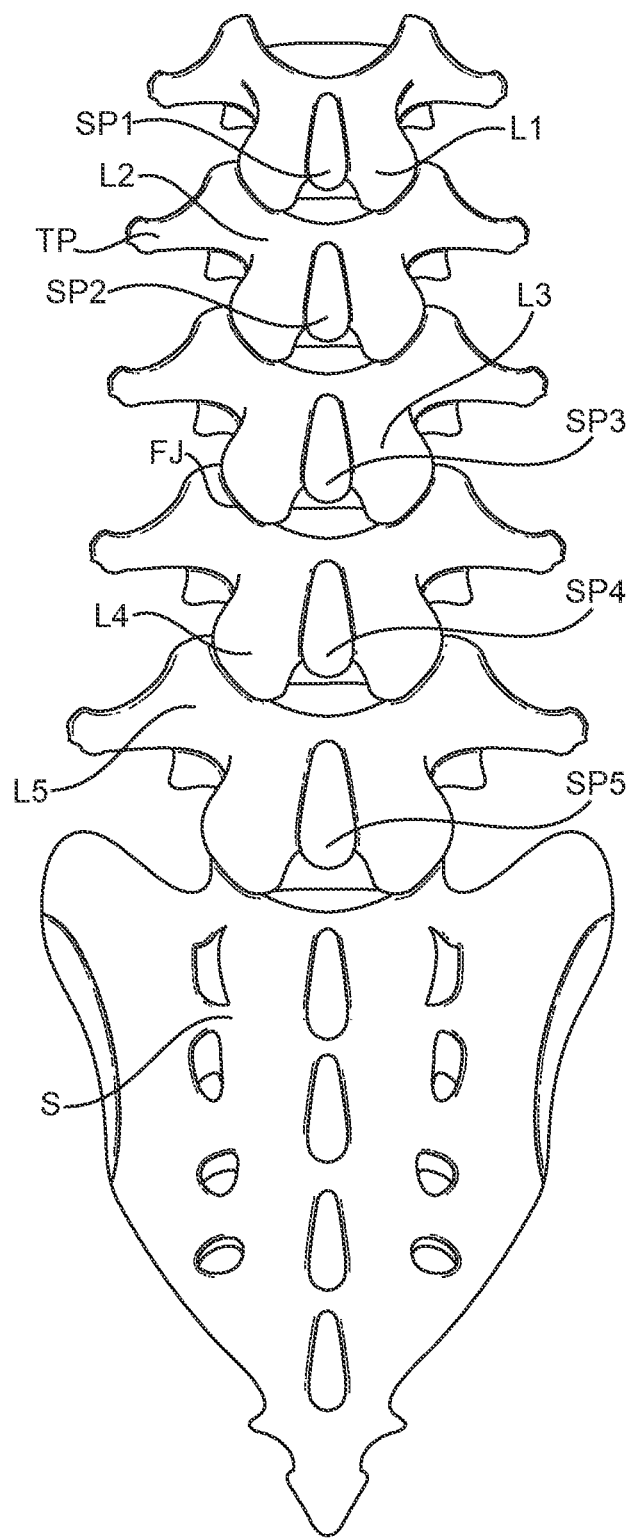
FIG. 1 is a schematic diagram illustrating the lumbar region of the spine.
Figure 1A:
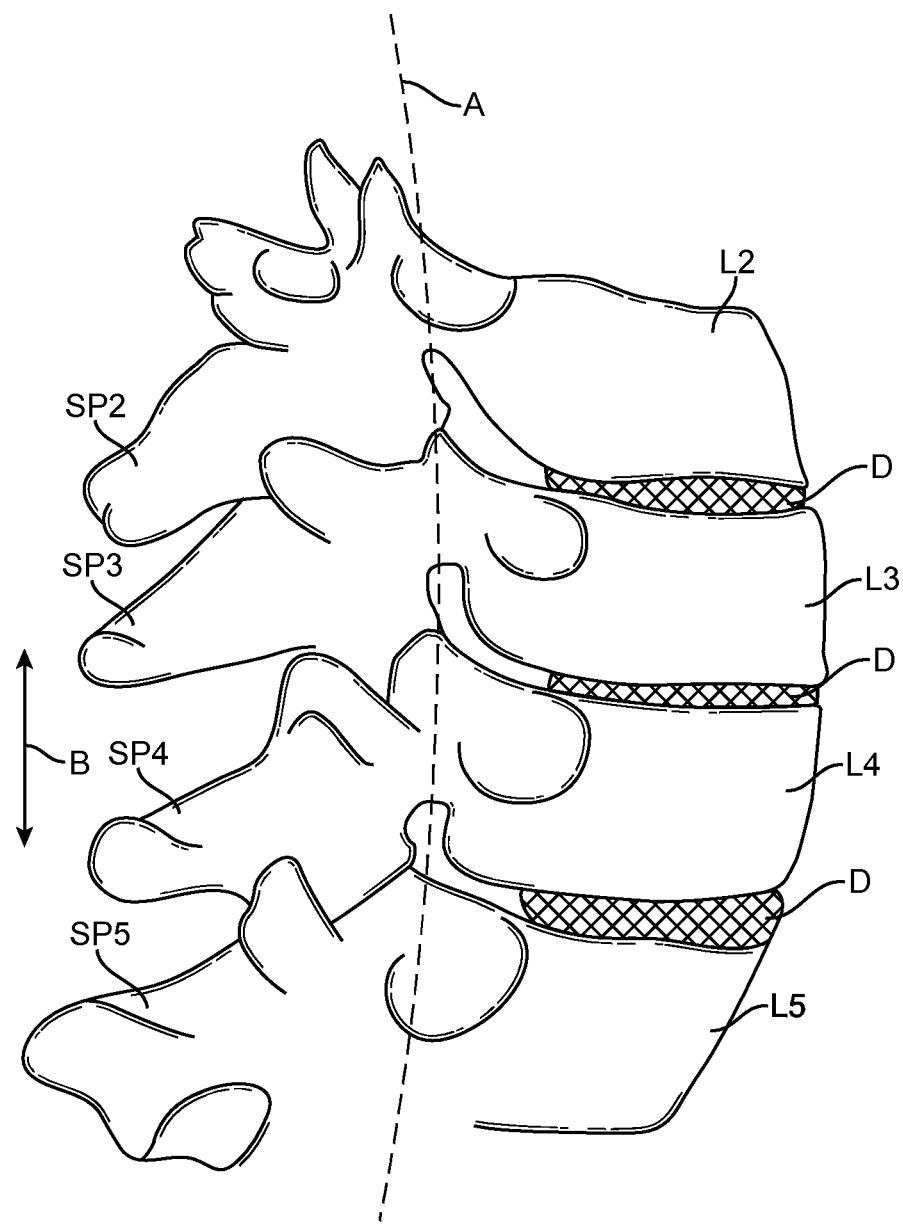
FIG. 1A a schematic illustration showing a portion of the lumbar region of the spine taken along a sagittal plane.

FIG. 1 is a schematic diagram illustrating the lumbar region of the spine including the spinous processes (SP), facet joints (FJ), lamina (L), transverse processes (TP), and sacrum (S). FIG. 1A is a schematic illustration showing a portion of the lumbar region of the spine taken along a sagittal plane and is useful for defining the terms "neutral position," "flexion," and "extension" that are often used in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the spine where the spine has a slight anterior convexity and slight posterior concavity. In some cases, the presence of the constraint of the present invention may modify the neutral position, e.g. the device may apply an initial force which defines a "new" neutral position having some extension of the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae in a spinal segment as the patient bends forward. Referring to FIG. 1A, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1A.

Additionally, as used herein, "extension" refers to the motion of the individual vertebrae L as the patient bends backward and the spine extends from the neutral position illustrated in FIG. 1A. As the patient bends backward, the anterior ends of the individual vertebrae will move apart. The individual spinous processes SP on adjacent vertebrae will move closer together in a direction opposite to that indicated by arrow B.

Figure 2:
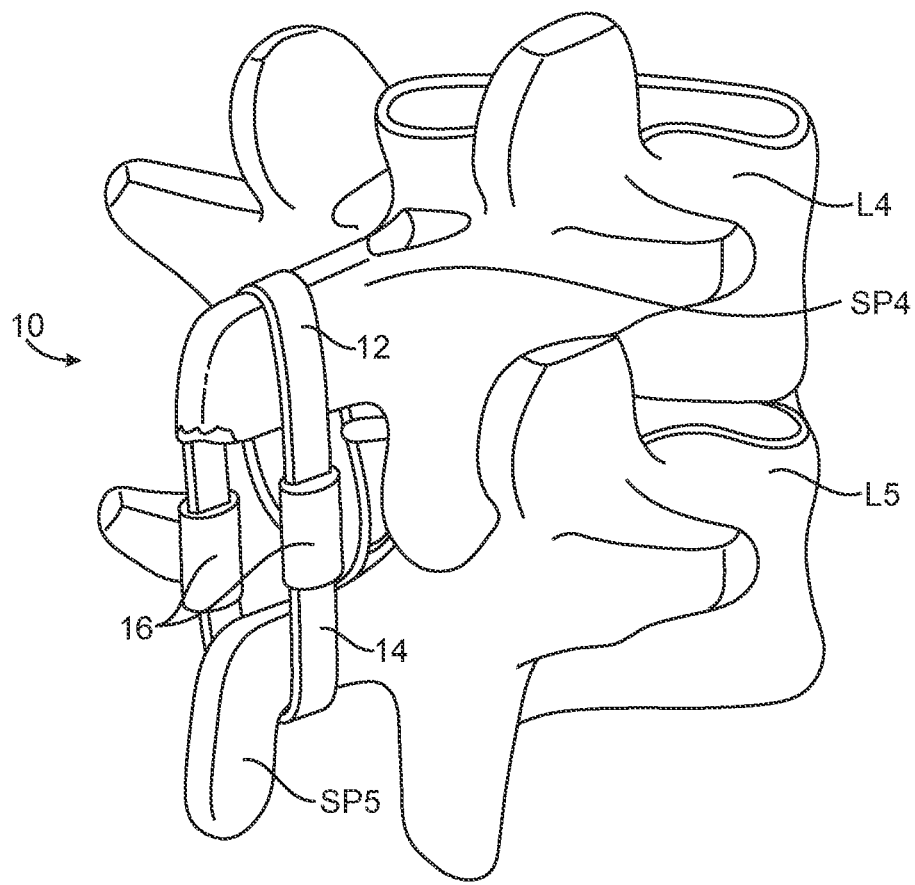
FIG. 2 illustrates a spinal implant of the type described in US Patent Publication No. 2005/0216017A1.

FIG. 2 shows a spinal implant of the type described in related U.S. Patent Publication No. 2005/0216017 A1 (now U.S. Pat. No. 7,458,981), the entire contents of which are herein incorporated by reference. As illustrated in FIG. 2, an implant 10 typically comprises an upper strap component 12 and a lower strap component 14 joined by a pair of compliance members 16. The upper strap 12 is shown disposed over the top of the spinous process Ser. No. SP4 of L4 while the lower strap 14 is shown extending over the bottom of the spinous process SP5 of L5. The compliance member 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which provides a force that resists flexion. The force increases as the processes move further apart. Usually, the straps themselves will be essentially non-compliant so that the degree of elasticity or compliance may be controlled and provided solely by the compliance members 16.

Figure 3A:
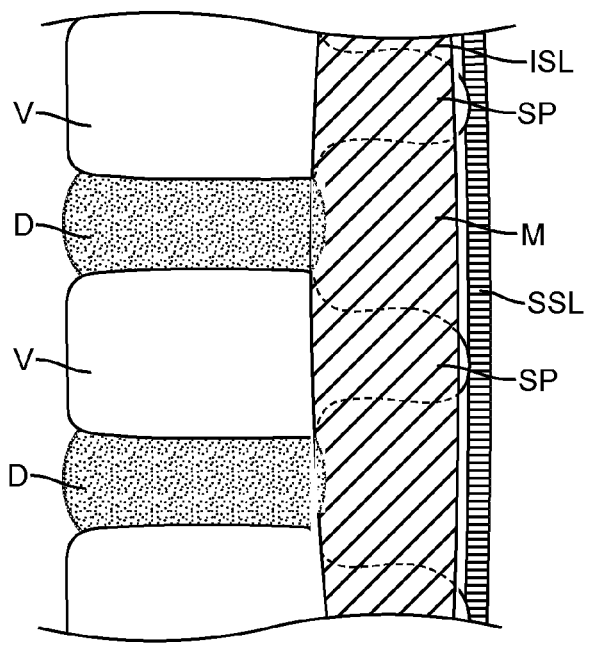
FIGS. 3A-3B illustrate additional tissue surrounding the spinous processes.
Figure 3B:
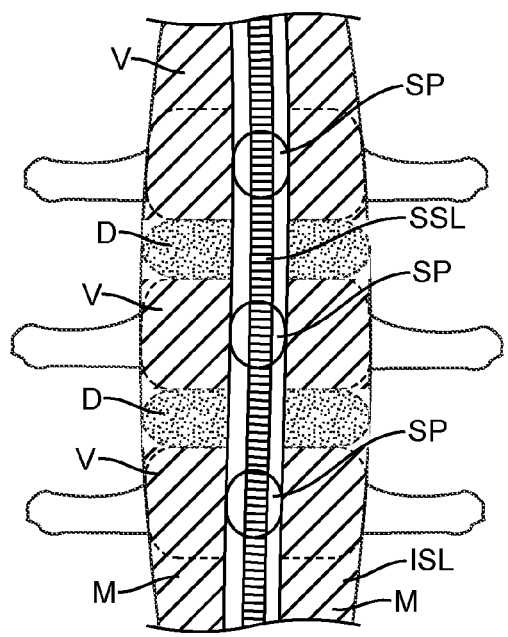

FIG. 3A is a side view of the lumbar region of the spine having discs D separating the vertebral bodies V. The supraspinous ligament SSL runs along the posterior portion of the spinous processes SP and the interspinous ligament ISL and multifidus tendon and muscle M run alongside of and attach to the spinous processes SP. FIG. 3B is a posterior view of FIG. 3A.

Figure 4A:
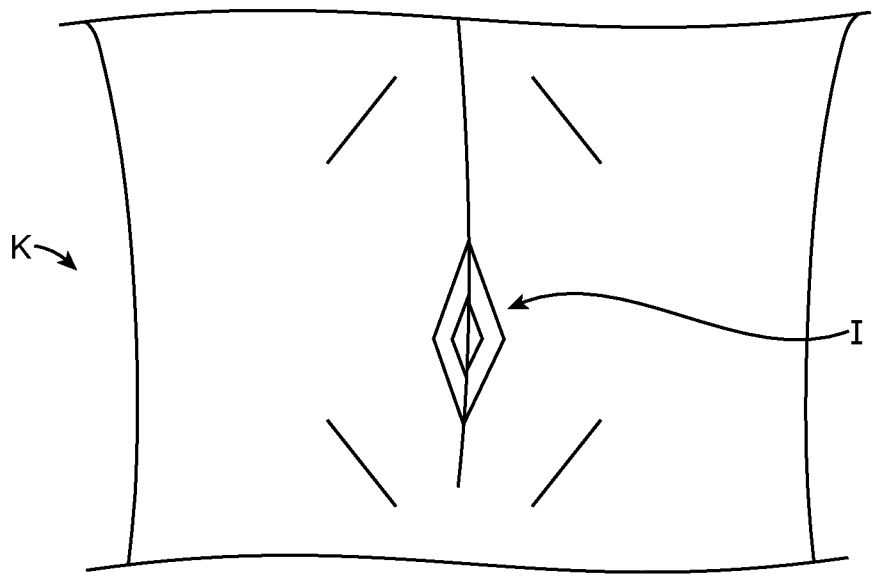
FIGS. 4A-4M show an exemplary method of surgically implanting a spinal device.
Figure 4B:
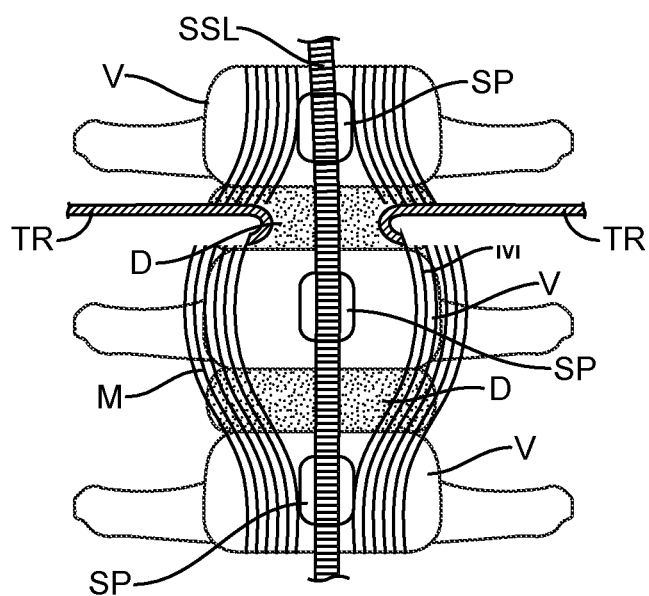

FIGS. 4A-4M illustrate an exemplary surgical method of implanting a spinous process constraint such as the embodiment of FIG. 2. One of the first steps to surgically implant a spinal implant is to make an incision to access the spinal area of interest. FIG. 4A shows the lumbar region of back K after an incision I has been made through the patient's skin. FIG. 4B illustrates the lumbar region of the spine after the incision I has been made through the patient's skin. Multifidus muscle and tendon M have been refracted with refraction tools TR to expose the spinous processes.

Figure 4C:
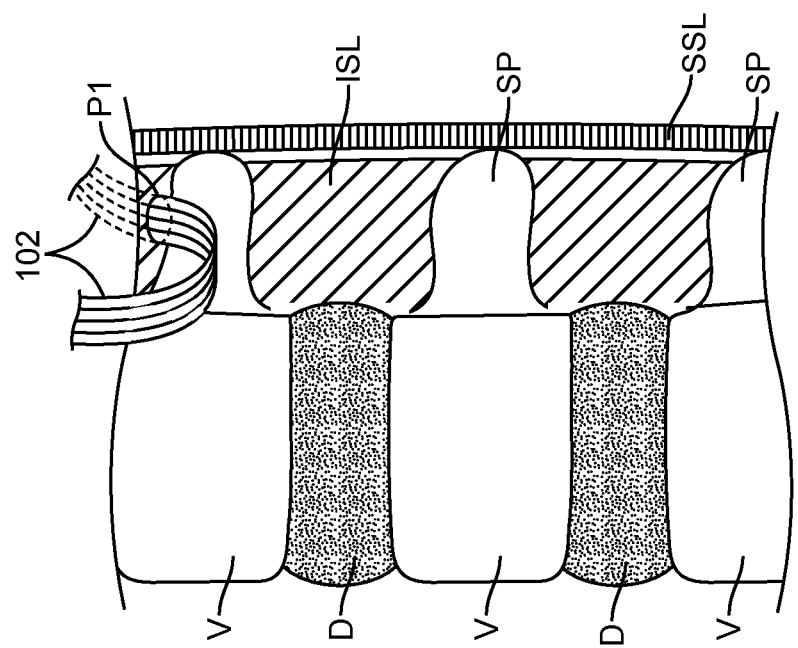
Figure 4D:
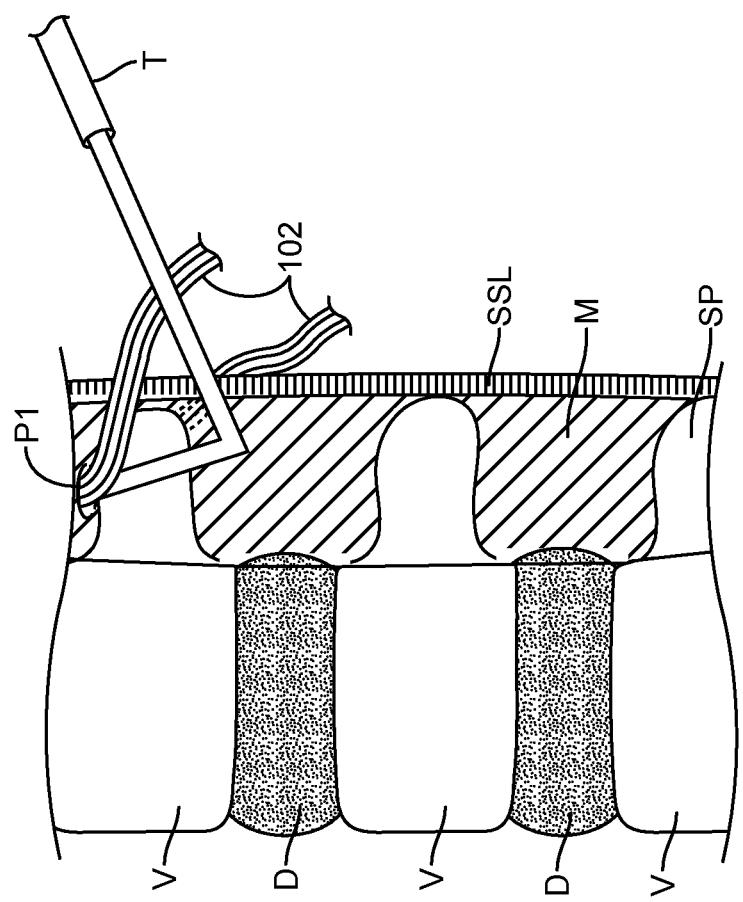

After the incision has been made, a piercing tool T having a sharp distal end may be used to access and pierce the interspinous ligament ISL while avoiding the supra spinous ligament SSL, creating an interspinous ligament perforation P1 superior of the first spinous process SSP of interest. This surgical approach is desirable since it keeps the supra spinous ligament intact and minimizes damage to the multifidus muscle and tendons and other collateral ligaments. As shown in FIG. 4C, from the right side of the spine, tool T accesses and pierces the interspinous ligament ISL adjacent of the first spinous process SSP of interest. The distal end of tool T is shown in dotted line. Alternatively, tool T may access and pierce the interspinous ligament ISL from the left side instead. The distal end of tool T is coupled with tether 102, parts of which are also shown in dotted line. In addition to accessing and piercing the interspinous ligament ISL, piercing tool T also advances or threads tether 102 through perforation P1. As shown in FIG. 4D, tool T is then removed, leaving tether 102 positioned through perforation P1. Multifidus tendon and muscle M is not shown in FIGS. 4C and 4D so that other elements are shown more clearly.

Figure 4E:
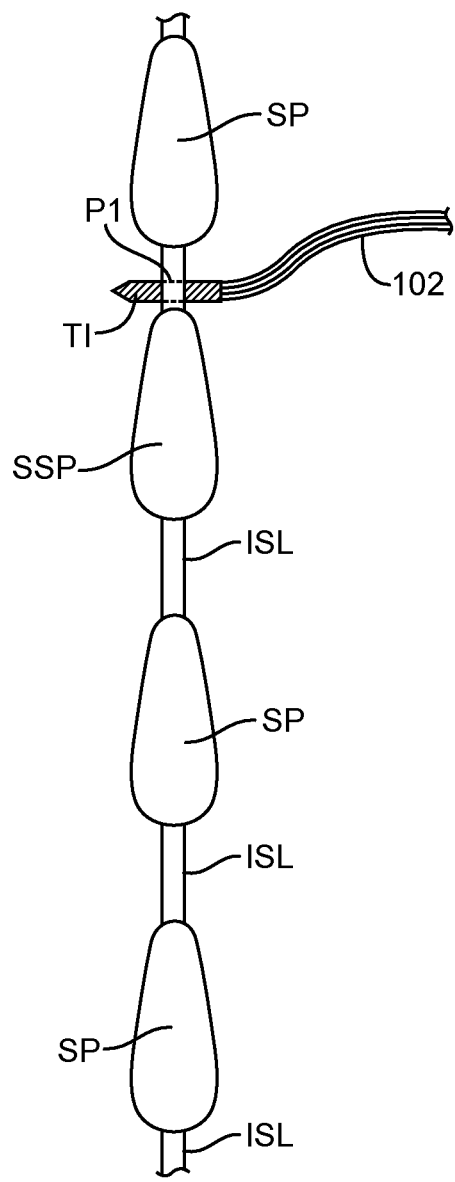

FIG. 4E is a posterior view of a section of the spine after the above steps have been performed. Often times, the distal tip TI of tool T is detachable. As shown in FIG. 4E, after tool T accesses and pierces the interspinous ligament ISL with distal tip TI, distal tip TI is detached from tool T and is left in place in perforation P1 (shown in dotted line) above the first spinous process SSP of interest. Tether 102 lags behind tip TI. In some cases, distal tip TI may fully pierce through interspinous ligament ISL. In these cases, distal tip TI has passed through the interspinous ligament ISL while a portion of tether 102 is left in place in perforation P1.

Figure 4F:
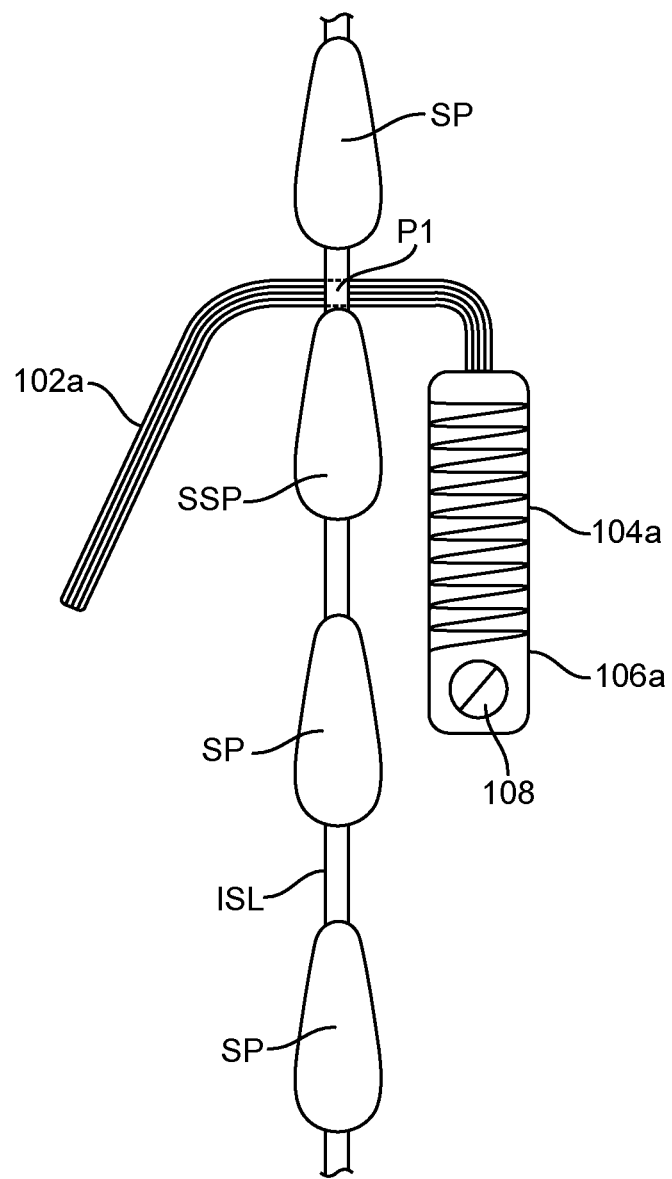

After tip TI or a portion of tether TH is left in place in perforation P1, another tool may couple with tip TI and pull tip TI such that it drags tether 102a and compliance element 104a to its appropriate position relative to the spine, as shown in FIG. 4F. Compliance element 104a is coupled to tether 102a and is used to provide a force resistive to flexion of spinous processes SP. Compliance element 104a includes a fastening mechanism or fastening element 106a (also referred to herein as a locking mechanism) and may further comprise a spring, a tensioning member, a compression member, or the like. Related compliance members are described in commonly owned U.S. patent application Ser. No. 12/106,103, the entire contents of which are incorporated herein by reference.

Figure 4H:
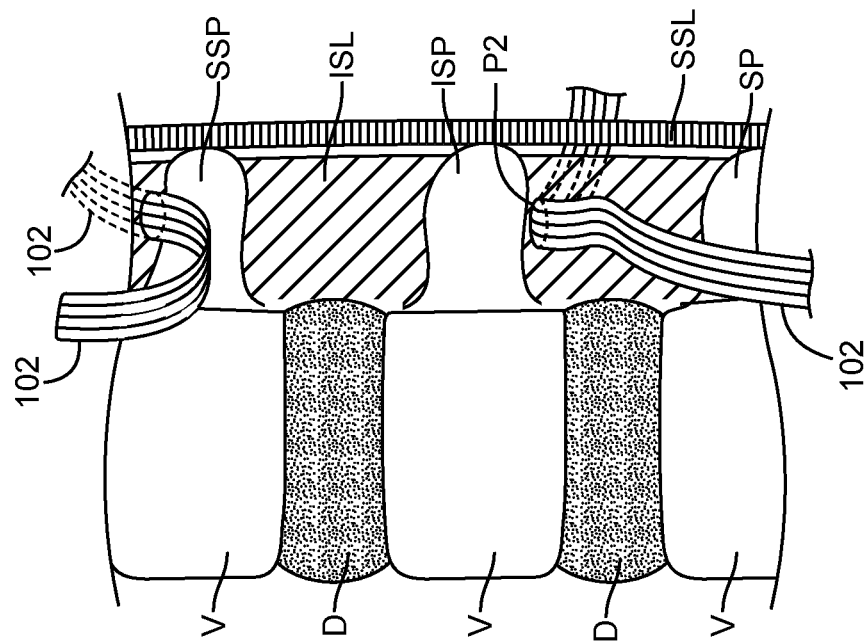
Figure 4G:
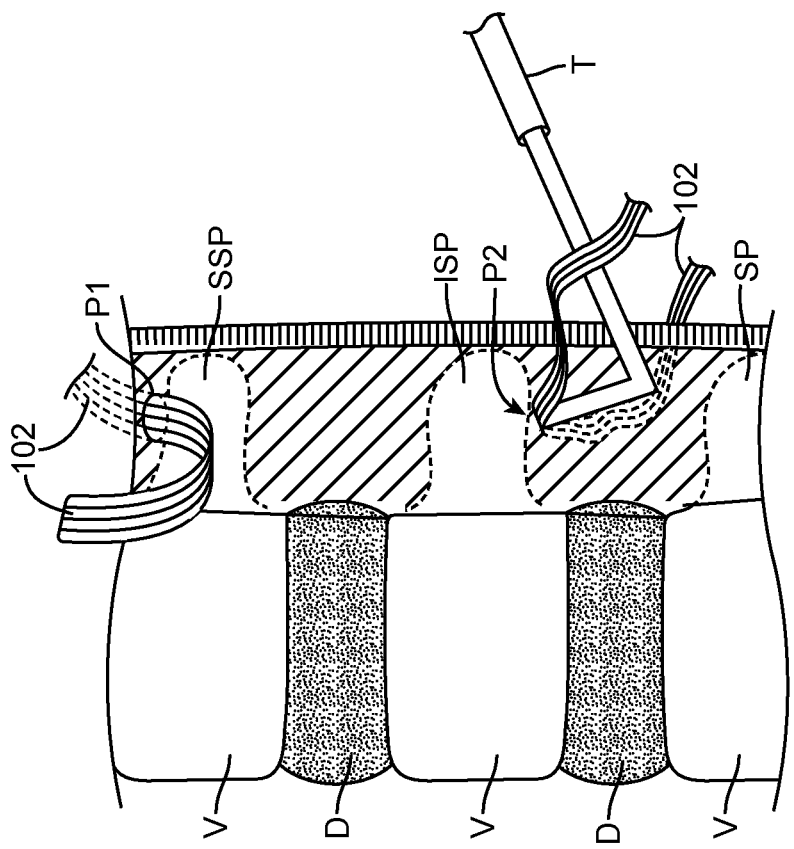

The steps of accessing the ISL, piercing the ISL, and threading tether 102 through a perforation are then repeated for the opposite, lateral side of the spine for an adjacent spinous process ISP, inferior of the first superior spinal process SSP of interest. As shown in FIGS. 4G and 4H, tool T accesses the interspinous ligament from the left side of the spinal midline and pierces the interspinous ligament ISL, creating a second perforation P2 located inferior of a second spinous process of interest, labeled as inferior spinous process ISP. As shown in FIG. 4G, the inferior spinous process ISP of interest is directly adjacent to and inferior of the first superior spinous process SSP of interest. However, it is entirely possible to perform the described procedure starting with the inferior spinous process ISP first instead of the superior spinous process SSP, for example, perforation P2 may be created before perforation P1. It is also possible that there may be a gap of one or more spinous processes SP between the spinous processes of interest. Multifidus tendon and muscle M is not shown in FIGS. 4G and 4H for clarity of the other shown elements.

Figure 4I:
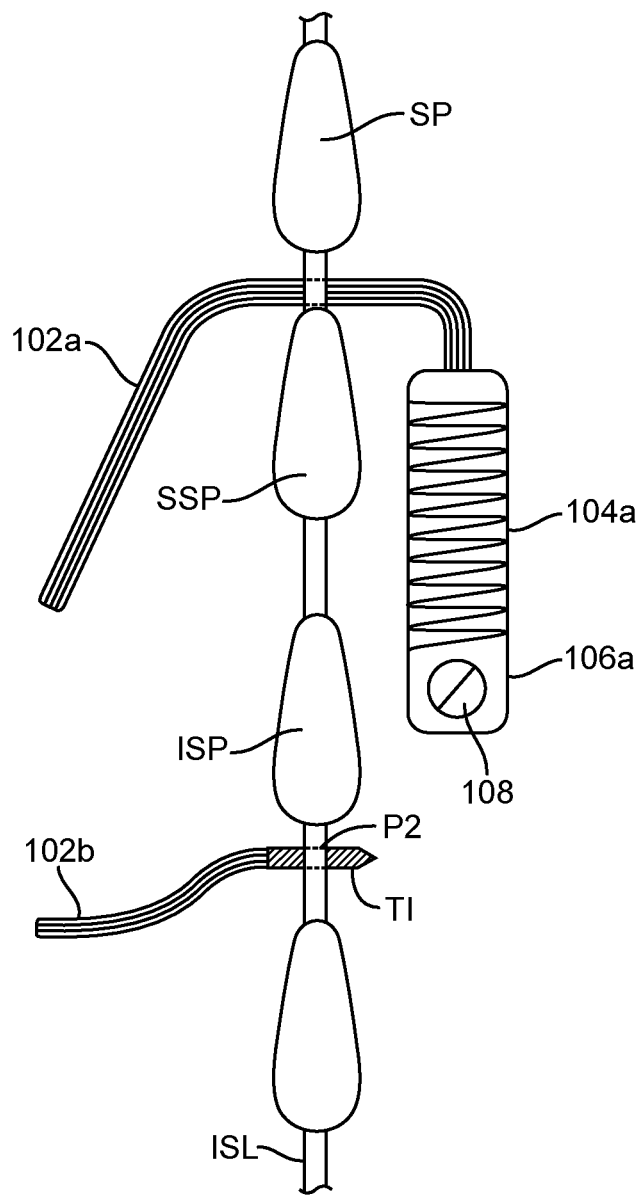
Figure 4J:
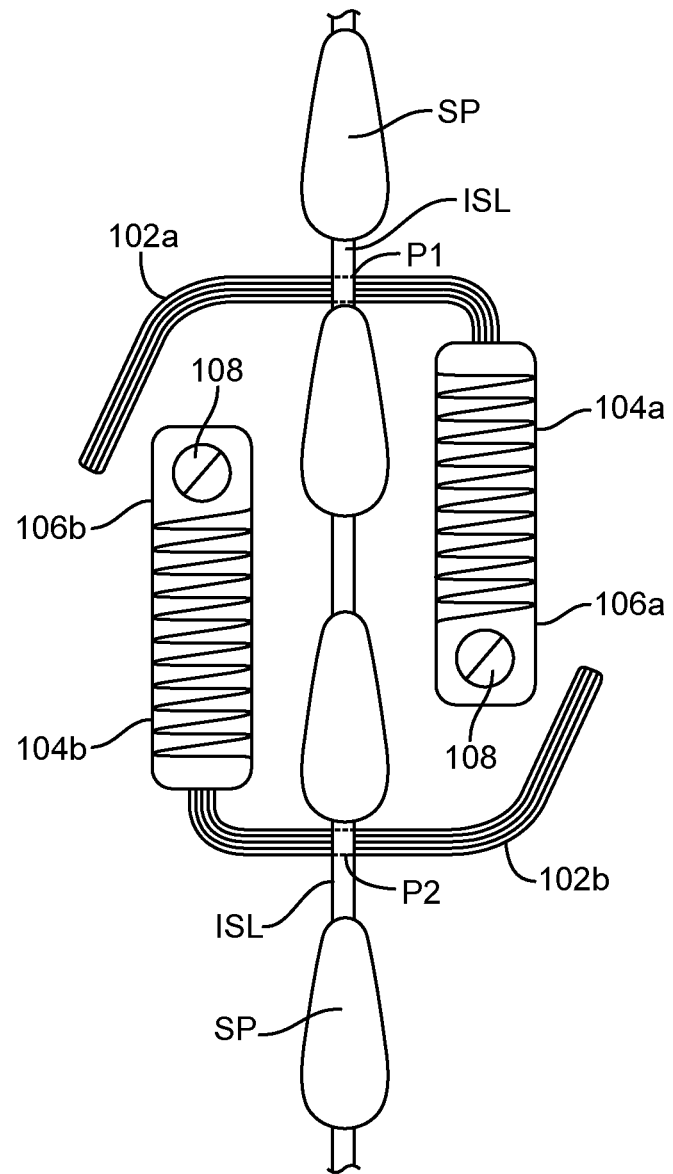
Figure 4K:
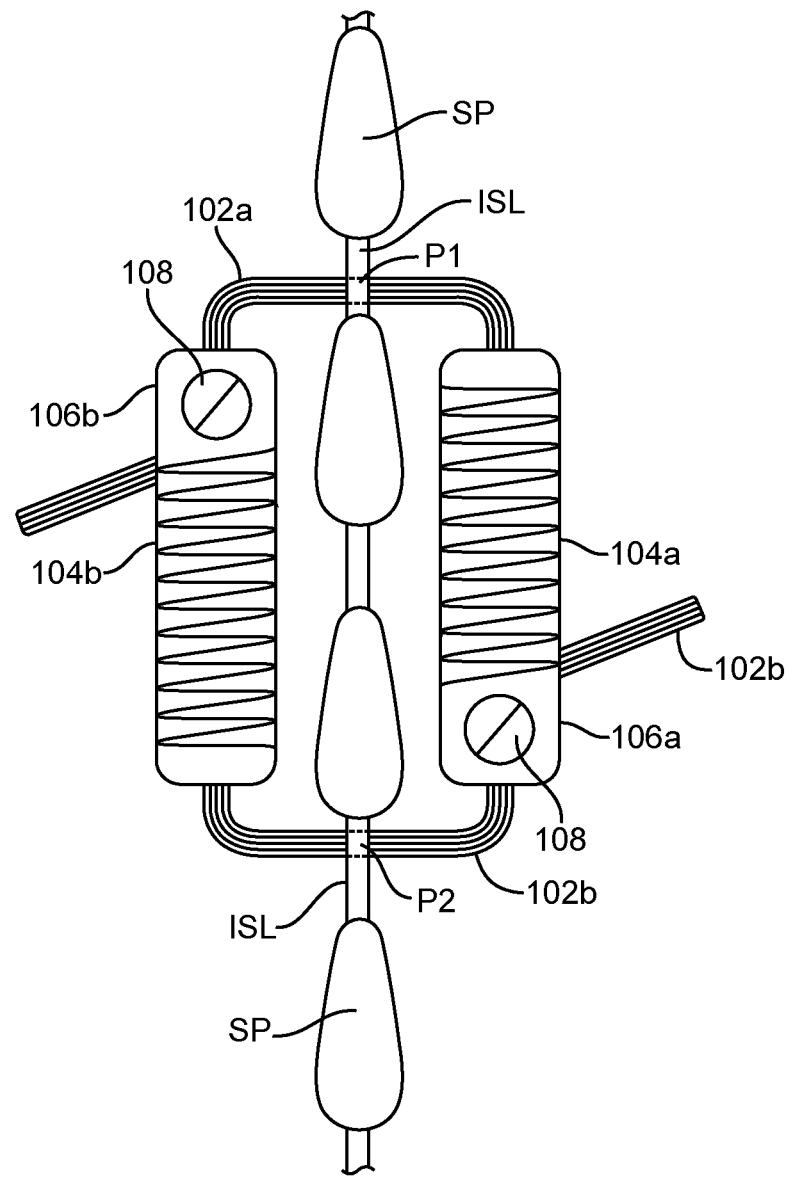

As shown in FIGS. 4H, 4I and 4J, like with the steps shown in conjunction with the first piercing, tether 102b is pierced through perforation P2 and left in place along with distal tip TI of tool T (best seen in FIG. 4I). Another tool such as a pair of forceps, is then used to grasp distal tip TI to pull tether 102b and compliance element 104b in place relative to the spine, as shown in FIG. 4J. Opposing compliance members 104a and 104b on opposite sides of spinous processes SP are oriented in opposite directions. Each compliance element 104a, 104b is coupled with their respective tether 102a, 102b and has a respective fastening mechanism or fastening element 106a, 106b. Fastening mechanism 106a, 106b are configured to couple with the tether 102a, 102b of the opposing compliance member 104a, 104b. For example as shown in FIG. 4K, tether 102a is advanced through compliance member 104b and is coupled with fastening mechanism 106b while tether 102b is advanced through compliance member 104a and is coupled with fastening mechanism 106a. Except for their orientation, compliance members 104a and 104b are identical. One of skill in the art will appreciate that the tether may enter and exit the fastening mechanism in a number of different directions and configurations, and FIG. 4K merely is one exemplary embodiment.

Figure 4L:
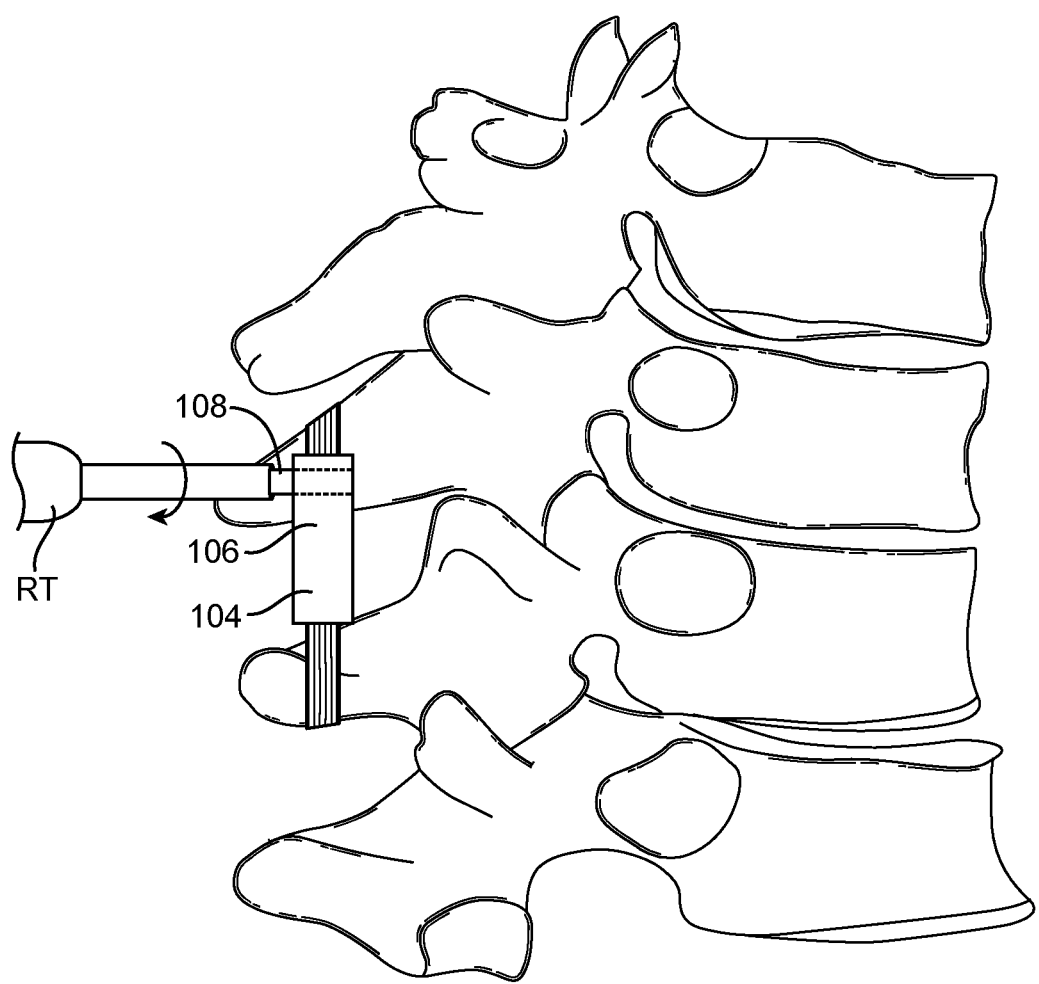
Figure 4M:
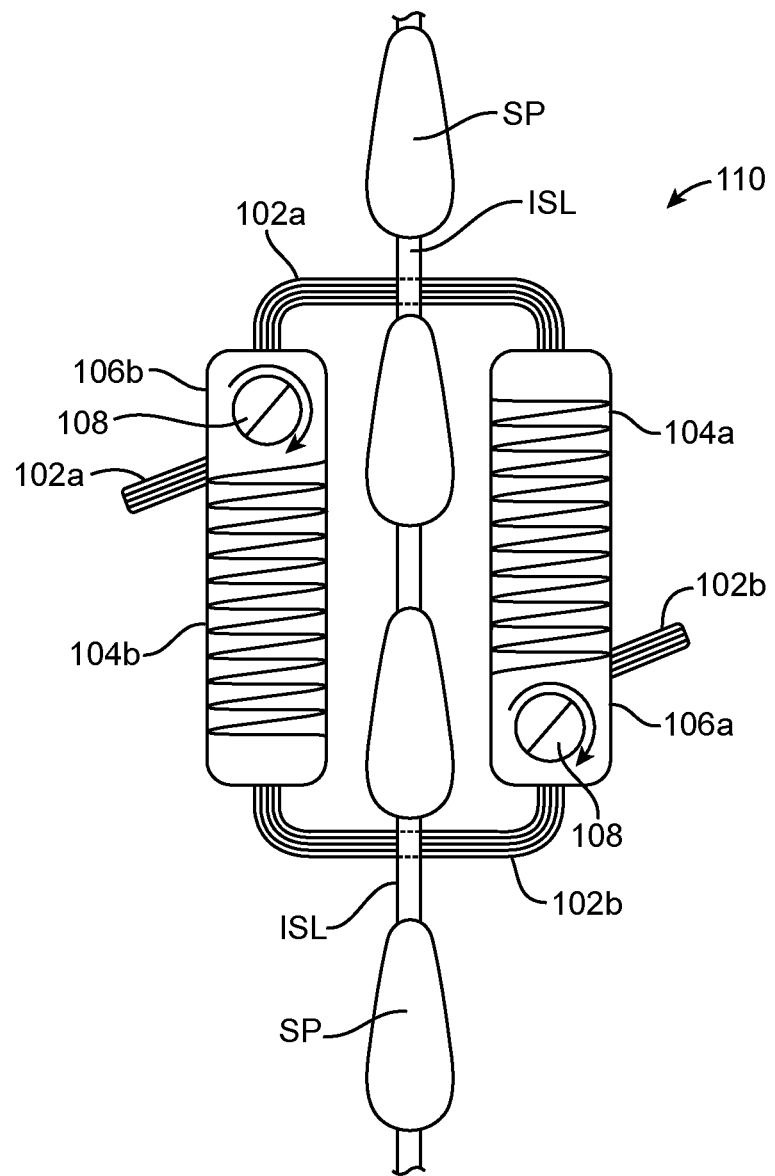

Fastening mechanism 106 (also referred to herein as a locking mechanism) may comprise a driver feature 108. As shown in FIG. 4L, the driver feature is adapted to receive a rotating driver tool RT. The driver feature may be a Phillips head, a slotted flat head, a Torx head, a hex head, or the like. Rotation of tool RT, which may be either clockwise or counter-clockwise, changes the configuration of fastening mechanism 106 so as to lock and secure tether 102 in place. This forms a continuous, multi-component tether structure or constraint 110 which couples two spinous processes SP together, as shown in FIG. 4M. Compliance elements 104a, 104b are used to control flexion between spinous processes SP while tethers 102a, 102b and respective fastening mechanisms 106a, 106b contribute to coupling the spinous processes SP together. Depending on the location of the perforations P1 and P2 and the lengths of the compliance elements 104a, 104b, constraint 110 may couple more than two spinous processes SP together. In general, compliance elements 104a, 104b comprise spring-like elements which will elastically elongate as tension is applied through tethers 102a, 102b in an axis generally parallel to the spine. As the spinous processes or spinous process and sacrum move apart during flexion of the constrained spinal segment, the superior tether 102a and inferior tether 102b will also move apart. Compliance elements 104a, 104b each include spring-like elements which will elastically resist the spreading with a force determined by the mechanical properties of the spring-like element. Thus, constraint 110 provides an elastic resistance to flexion of the spinal segment beyond the neutral position. Constraint 110 is often configured to provide a resistance in the range from 7.5 N/mm to 20 N/mm but the resistance may be below 3 N/mm or even below 0.5 N/mm Constraint 110 may also be adjustable in certain dimensions to allow tightening over the spinous processes or spinous process and sacrum when the spinal segment is in a neutral position. Other, related tether embodiments and joining methods are disclosed in U.S. patent application Ser. No. 12/106,103, U.S. Patent Publication No. 2008/0009866, U.S. Patent Publication No. 2008/0108993, U.S. patent application Ser. No. 12/106,049 and U.S. Provisional Patent Application No. 60/936,897, each of which, the entire contents are incorporated herein by reference.

Figure 5:
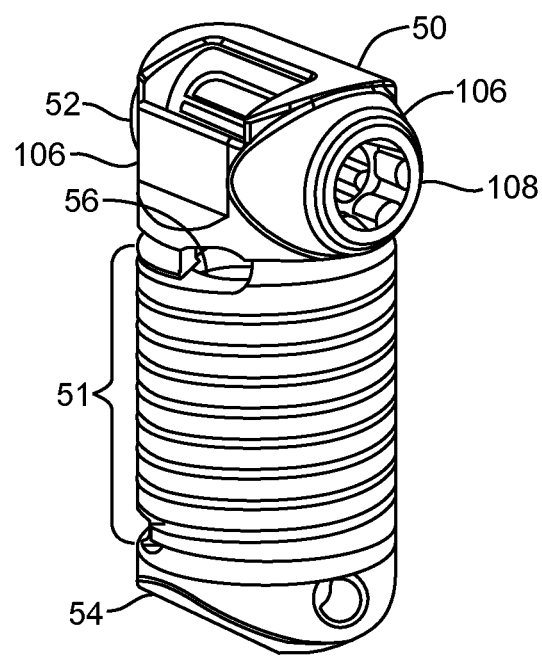
FIG. 5 illustrates an exemplary compliance element.

FIG. 5 illustrates an exemplary embodiment of a spring-like element 50 of compliance member 104a, 104b. Spring-like element 50 is generally similar to the spring-like elements disclosed in related, co-assigned U.S. patent application Ser. No. 12/106,103, the entire contents of which are incorporated herein by reference. Fastening mechanism 106 having a driver feature 108 is housed within spring-like element 50. Element 50 comprises a housing having a helical groove machined in the housing body to form the spring-like element. Element 50 includes an adjustable tether connector 52 and a fixed tether connector 54, both of which are preferably formed integrally or monolithically with the helical spring structure 51. Typically, the helical spring structure 51 and coupling portions of both tether connectors 52 and 54 will be formed from one piece of material, usually being a metal such as titanium, but optionally being a polymer, ceramic, reinforced glass or other composite, or other material having desired elastic and mechanical properties and capable of being formed into the desired geometry. In a preferred embodiment, spring-like element 50 is machined or laser cut from a titanium rod. Alternatively, a suitable polymeric material will be polyetherether ketone (PEEK). Other features may be built into the spring-like element 50, such as a stress relief hole 56. Components that compose the adjustable tether connector may potentially include a roller and a lock-nut; such components could be made from the same material as the element 50 and adjustable tether connector (e.g. titanium components if the spring-like element 50 is titanium), or they could be made from a different material (e.g. injection molded PEEK). The exterior of the spring-like element 50 may be covered with a protective cover, such as a sheath fabricated from an elastomer, polymer or other suitable material. The sheath may be placed over the body of the spring-like element 50 in order to prevent the intrusion of tissue and body fluids into the spaces between the turns of the coil and interior of the element.

Figure 6A:
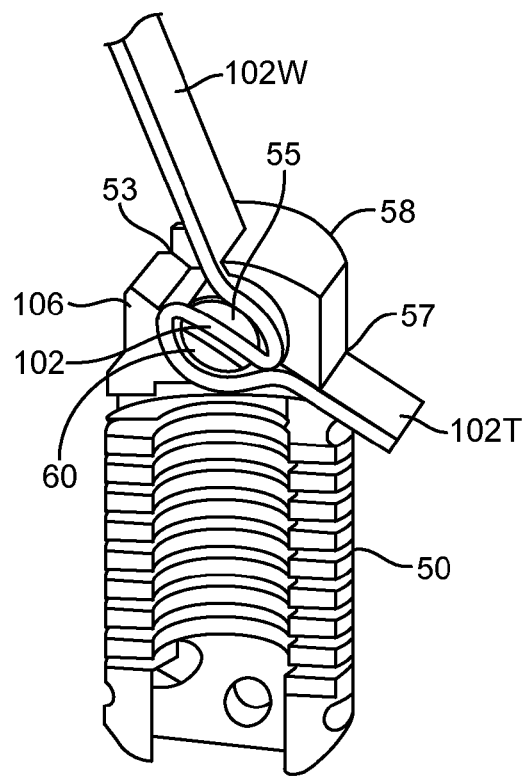
FIGS. 6A-6C illustrate the use of an exemplary fastening or locking mechanism incorporated in the compliance element for removably locking a tether.

FIG. 6A shows a cross-section of spring-like element 50 having tether 102 locked therein. Tether 102 enters and exits the housing 58 of fastening mechanism 106 through entry aperture 53 (also referred to herein as a slot), then it passes through central channel 55 (also referred to herein as a slot), winds around roller 60 and the inside surface of housing 58, and finally exits through exit aperture 57 (also referred to herein as a slot). Roller 60 is housed within central channel 55 and is rotatable within tension element 50. Roller 60 is often substantially cylindrically shaped but may also have other shapes, for example, an eccentric shape. A round symmetrical roller will allow the tether 102 to spool evenly from both the working end and the tail end of the tether 102, while an eccentrically shaped roller will result in uneven spooling. The housing 58 of fastening mechanism 106 may be formed integrally with spring-like element 50 or may be separate.

Figure 6B:
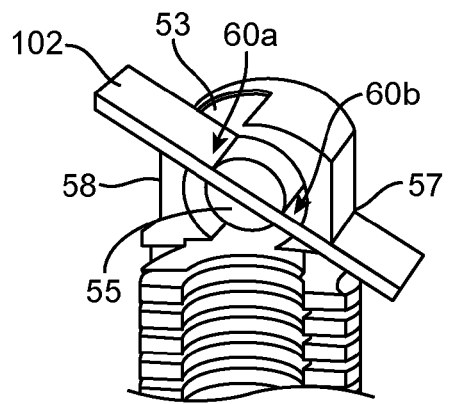
Figure 6C:
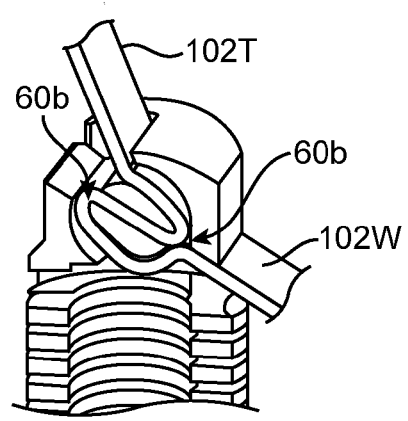

During a procedure similar to the one described with reference to FIGS. 4A-4M, tether 102 is advanced through top aperture 53, central channel 55 and roller 60, and out through bottom aperture 57. As shown in FIG. 6B, top aperture 53, central channel 55, and bottom aperture 57 are aligned so permit easy passage of tether 102 therethrough. Roller 60 includes two side apertures 60a, 60b. Prior to the locking of the tether, entry aperture 53, side apertures 60a and 60b and exit aperture 57 are all aligned along a common axis. To provide such alignment, roller 60 may include an alignment feature such as a pin or shoulder. Thus, the roller 60 may be rotated until stopped by the pin or shoulder, thereby ensuring alignment of all the apertures. Once tether 102 is advanced through, roller 60 is rotated, via driver feature 108, thus creating a friction-based interference fit between roller 60, the inside surface of the housing and the tether 102. As shown in FIG. 6C, the fastening mechanism is rotated approximately 180° to create this fit. The rotation of the roller creates a tortuous path for the tether as it passes between side apertures 60a, 60b. The rotation may retract the working end 102w and tail end 102t of tether 102, sometimes of different lengths, inward toward roller 60. Offsetting roller 60 from its axis of rotation by using an eccentrically shaped roller changes the amount of tether drawn from either side. The roller may also be rotated a selected amount in order to draw a desired amount of the tether into the roller. For example, the roller may be rotated from about ¼ turn to two or more complete revolutions. Thus, not only will the locking mechanism secure the tether in position, but it may also be used to help adjust length or tension of the tether.

A friction-based interference fit is advantageous because the range along the tether to which the mechanism can attach is continuous, rather than in discrete increments of non-friction mechanisms such as teeth, hooks, loops, and the like. Thus, forces between roller 60 and tether 102 are distributed along a longer portion of tether 102. Additionally, high clamping forces are not required. Thus, the risk that any specific point of contact will abrade, wear, or will otherwise be damaged is minimized. Furthermore, in contrast with other mechanisms that require high clamping forces, the discrete rotation of a tool is easier and more repeatable to perform during surgery.

After the tether is secured, roller 60 is then locked in place. Various means may be provided to lock roller 60 in place within housing 58. Roller 60 and/or the inner surface of housing 108 may include male or female threads which engage the two elements together. The threads may be partially deformed, thereby helping to secure the roller element with the housing. Alternatively, a pin 73 may be coupled to housing 58 and roller 60 may comprise a groove adapted to receive pin 73. Another possibility is that housing 58 may include a flange adapted to retain roller 60. A set screw as described below with reference to FIG. 7 may also be provided to lock roller 60 in place. Rotation of roller 60 in the opposite direction unwinds tether 102 from roller 60 and reduces the interference fit. Roller 60 and/or housing 58 may further include a position indicator, such as detents or calibration marks, to provide visual, tactile, or audible feedback to an operator on the relative position of the roller with respect to housing 58.

Figure 7:
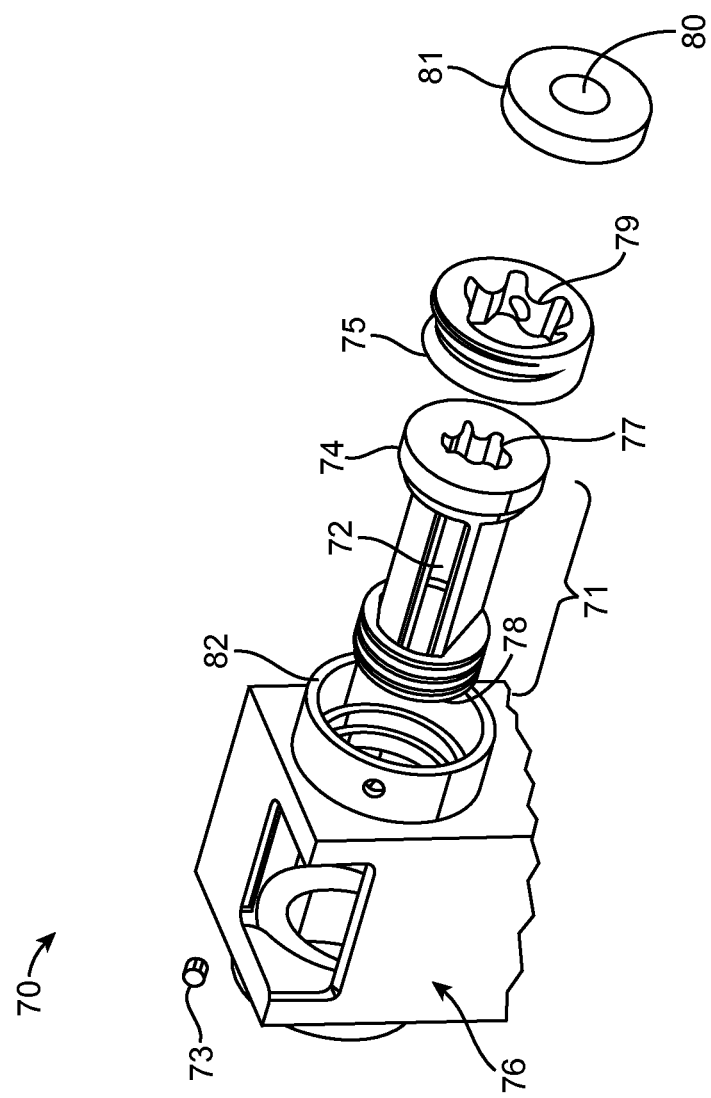
FIG. 7 is an exploded view of an exemplary fastening or locking mechanism.

FIG. 7 shows an exploded view of an exemplary fastening mechanism 70 that uses a locking set screw 75 to lock roller 76 in place. Roller 71 is generally similar to roller 60. It is positioned within housing 76 and includes slots 72 for a tether to be advanced through. Roller 71 has threads 78 on one end that may be threadably engaged with the housing 76. Roller 71 also has a shoulder 74 and includes driver features 77. Shoulder 74 is adapted to be engageable with locking set screw 75 and housing 76. After roller 71 has been rotated to lock and secure a tether in place, set screw 75 is set in a position to engage roller 71 with housing 76 and hold it in position relative to housing 76. Shoulder 74, set screw 75, and/or housing 76 have threads to allow such engagement. The threads may be partially deformed, thereby further securing the locking member with the housing. The threads prevent the roller 71 from unrolling thereby allowing release of the tether. Set screw 75 may comprise driver features 79 to allow rotation of the set screw. Driver features 77 of roller 71 and driver features 79 of set screw 75 each are adapted to receive a tool so as to permit rotation thereof. The driver features 77, 79 may be a Phillips head, a slotted flat head, a Torx head, a hex head, or the like. Driver features 79 of set screw 75 may comprise an aperture large enough to permit access to roller 71 with a tool that can rotate roller 71 while set screw 75 is engaged with housing 76. An optional end cap 81 having a central aperture 80 may be positioned adjacent the set screw 75 and welded, bonded or otherwise affixed to the outer rim 82 of the housing 76 so as to capture all the components forming an inseparable assembly. The aperture 80 is sized to allow access to rotation of the set screw. This is desirable since it prevents parts from falling out during use and also provides a device which is easier to use since assembly is not required. In preferred embodiments, the assembly may not be disassembled without breaking or otherwise damaging the device. In other embodiments, the assembly may be disassembled without damaging the device.

One advantage of the roller locking mechanisms disclosed herein is that the tether is not deformed in planes in which it lies. The tether may be folded or rolled in a plane transverse to the planes in which it lies. This is desirable since it minimizes the possibility of twisting or tangling of the tether and also reduces wear and tear.

Figure 8B:
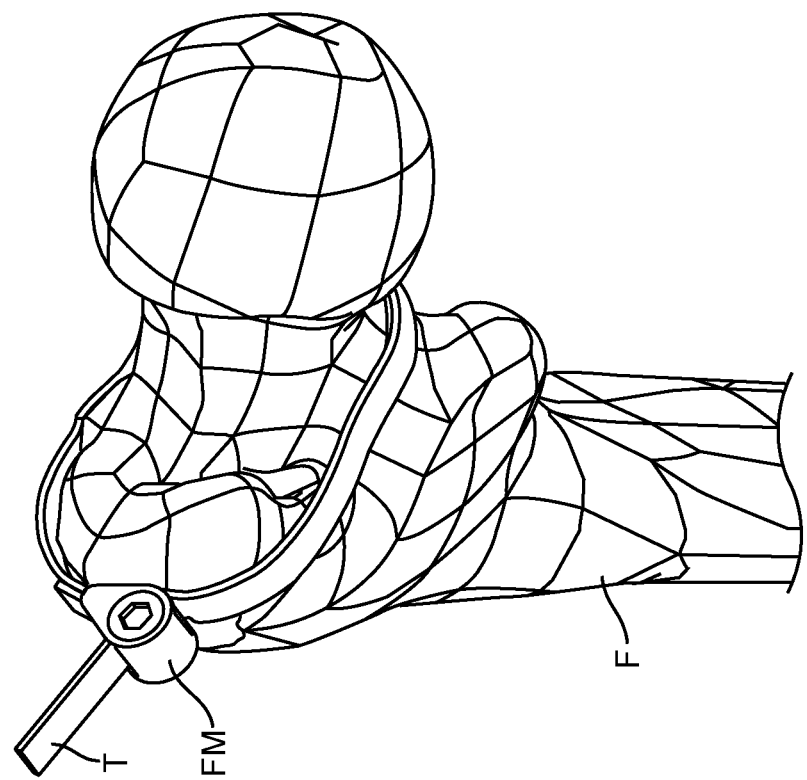
FIGS. 8A-8B illustrate the use of a tether and a fastening or locking mechanism in trochanteric fracture fixation.
Figure 8A:
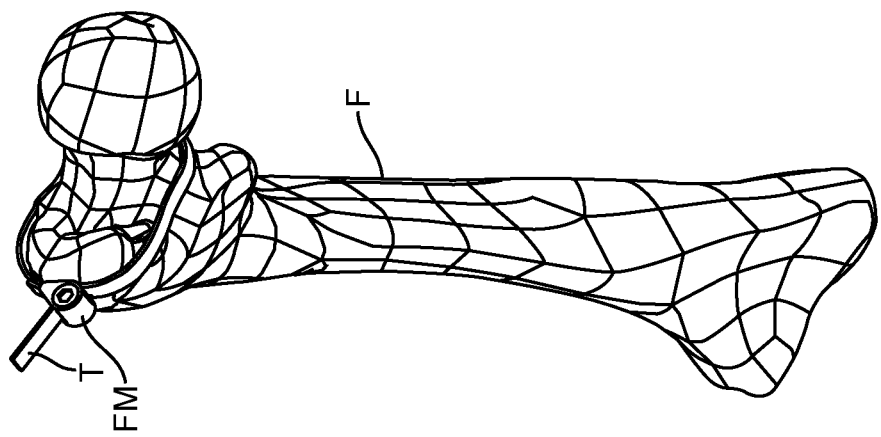

While the exemplary embodiments described above illustrate a fastening mechanism that is coupled with a spring-like compliance member, one will appreciate that the fastening mechanism may be used independently of a spring or other internal fixator. Other uses may include applications where a tether is secured with a knot, crimped or the like. These may include cerclage applications such as in trochanteric fixation in addition to application of a substantially rigid tether to multiple spinous processes or lamina. FIGS. 8A-8B illustrate the use of a tether and fastening mechanism for trochanteric fixation. FIG. 8A shows a tether T wrapped around the trochanter of a femur F. A fastening mechanism FM releasably locks one end of the tether T, thereby forming a closed loop around the trochanter. FIG. 8B highlights the tether wrapped around the trochanter.

In addition to the flexion limiting device and locking mechanism described above, various other accessory items may be useful for delivering and adjusting the device during the minimally invasive surgical procedure. The embodiments described below may be used alone or in combination with any of the tether and locking mechanisms described here. Several of these are disclosed below.

Indicator Plate:

Actuating the locking mechanism previously described above is preferably accomplished with a tool having an inner driver (also referred to as a locking instrument) and an outer driver (also referred to as a stopping instrument). The inner driver actuates the roller and an outer driver actuates the locking set screw. The inner driver is preferably disposed in a central channel of the outer driver. Because the implant device preferably has two compliance members, four drivers may be required to secure the tether in a desired configuration (two inner drivers and two outer drivers). This can create confusion for an operator as to whether a driver has been actuated and which direction to actuate the driver. Thus, it would be desirable to provide an indicator plate that indicates the direction to actuate the instruments, as well as indicating how far to actuate the instrument, and locking mechanism status. FIGS. 9A-9I illustrate exemplary instruments and methods for implanting the tether, actuating the locking mechanism, and for monitoring status of the locking mechanism.

Figure 9A:
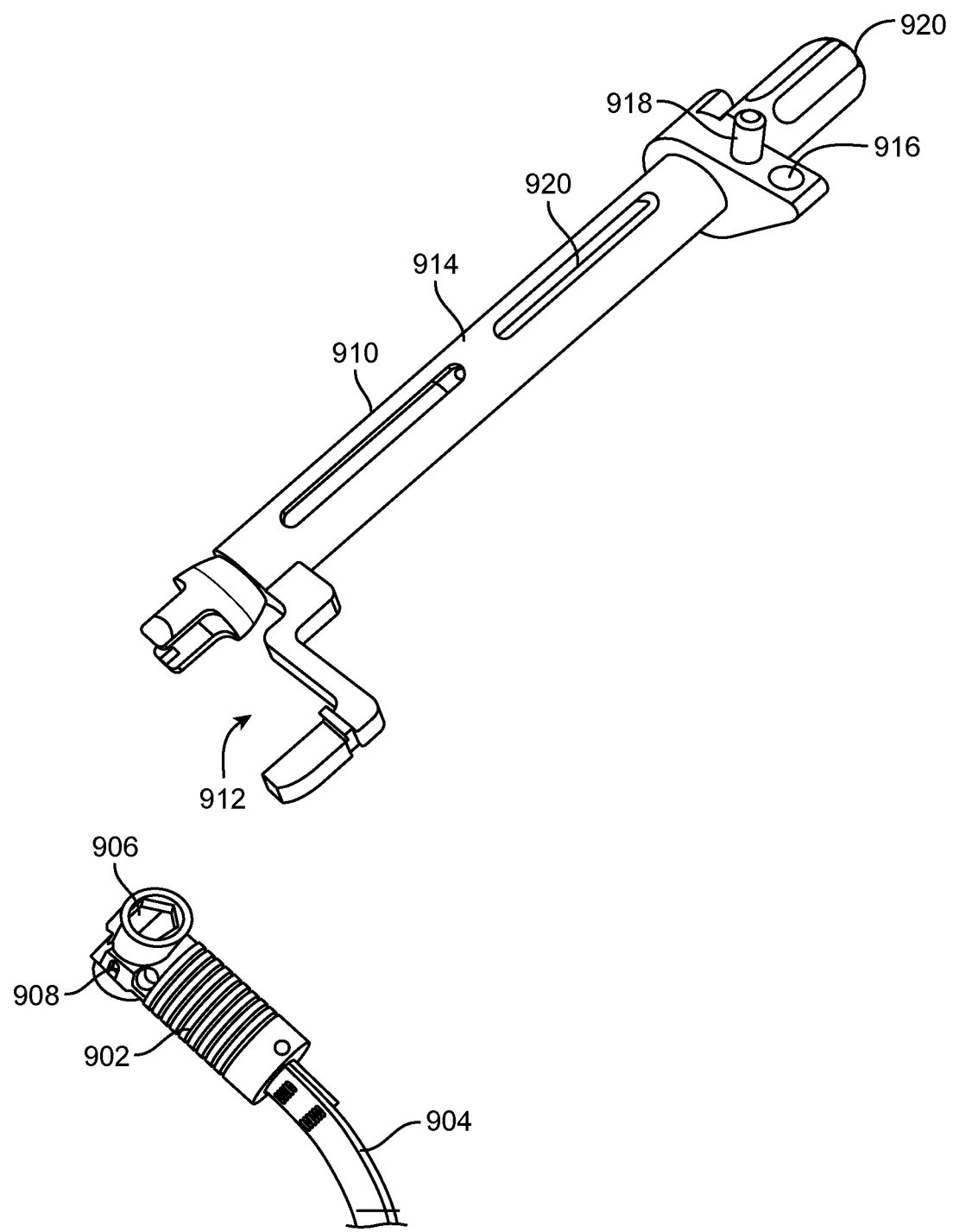
FIGS. 9A-9I illustrate use of an indicator plate.

FIG. 9A illustrates a tether 904 coupled to a compliance member 902 having a locking mechanism 906 for locking the tether 904 in a slot 908 of the locking mechanism. Because the compliance member can expand and contract during adjustment of loop size or loop tension, a holding instrument 910 having an elongate shaft 914 with a cradle 912 on the distal end can be used to hold the compliance member 902 during implantation without undesirable contraction or expansion of the compliance member. A pin 918 and slot 916 near the proximal end of the elongate shaft 914 allow a second adjacent holding instrument with mating pin and slot to be coupled together. A textured handle on the proximal end of the elongate shaft 914 allows the handle to be firmly grasped and manipulated. The elongate shaft preferably has a central channel 920 that allows instruments to be passed therethrough for access to the locking mechanism 906.

Figure 9B:
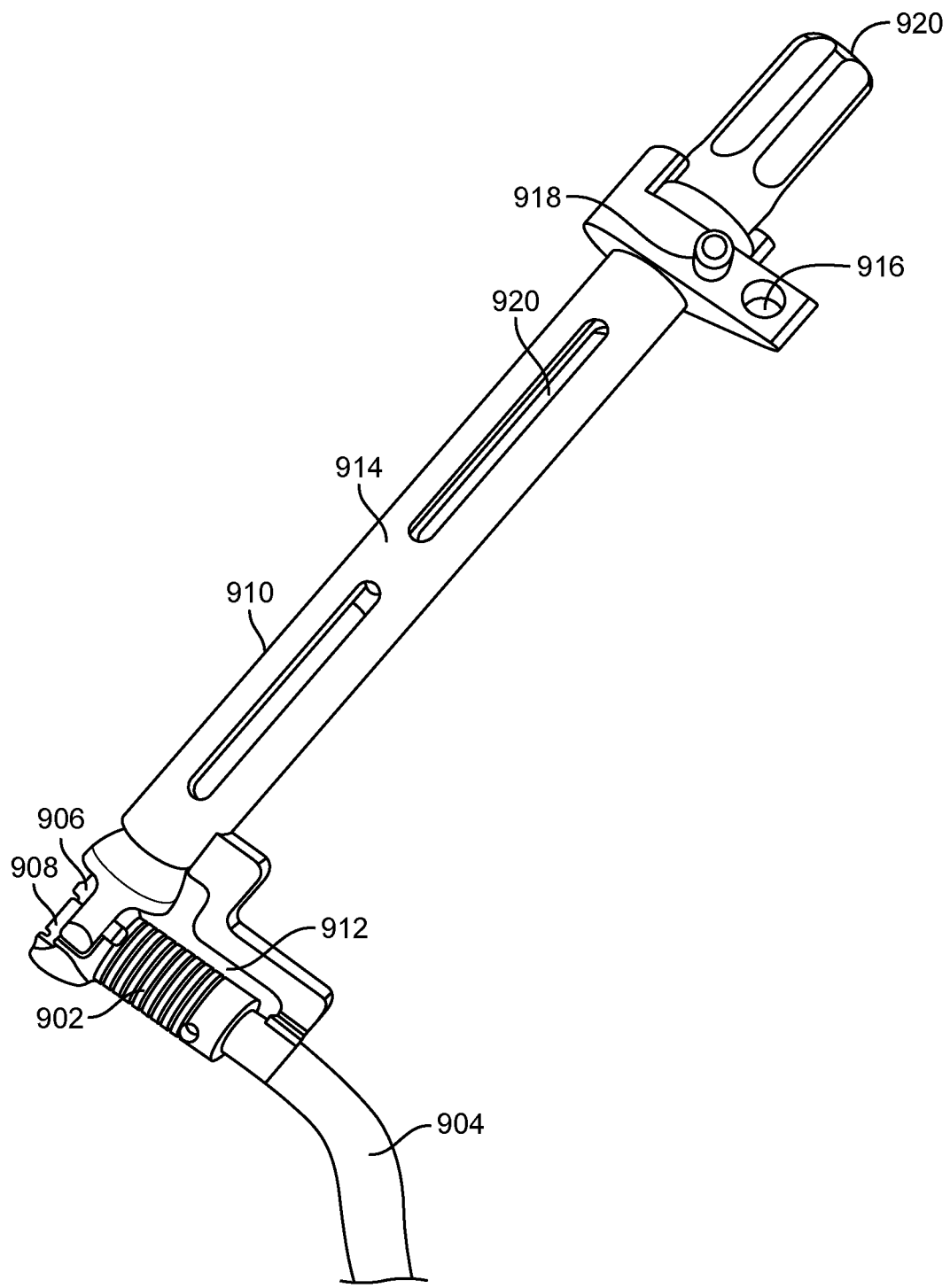
Figure 9C:
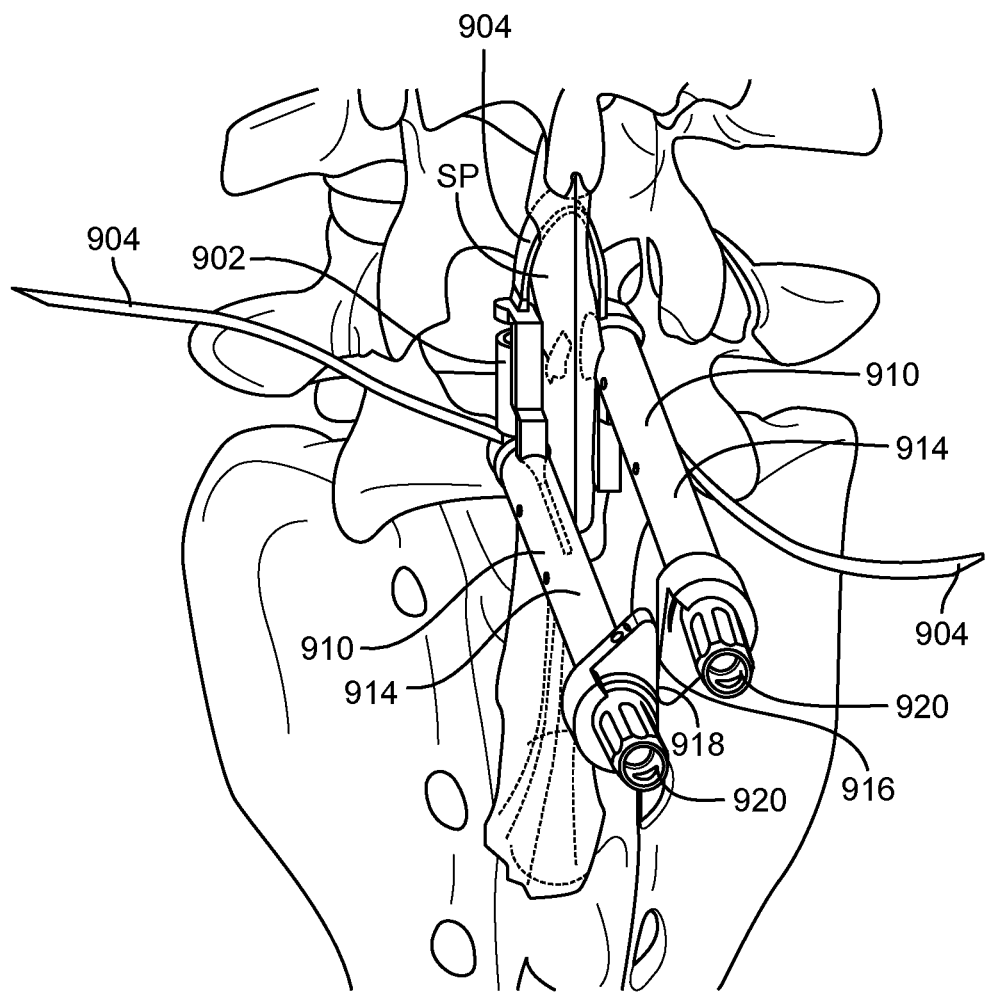

FIG. 9B illustrates cradling of the compliance member 902 in the cradle 912. Additional details on the cradle are disclosed in U.S. patent application Ser. No. 13/037,039, the entire contents of which are incorporated herein by reference. The compliance member is positioned so that the locking mechanism is lined up with the central channel 920, thus instruments may be inserted into the central channel to engage and actuate the locking mechanism. FIG. 9C illustrates two holding instruments 910 each having a compliance member 902 disposed on opposite sides of the spinal segment midline with a portion of the tether 904 passing through the interspinous ligament and disposed over a superior surface of a superior spinous process, and another portion of tether 904 passing through the interspinous ligament and disposed over an inferior surface of an inferior spinous process using the methods described previously above. The two holding instruments are coupled together near their proximal ends because the pin 918 on one instrument is received in the slot 916 on the adjacent instrument, and similarly the pin on the other instrument is received in the corresponding slot in the first instrument. The two holding instruments are then disposed vertically and substantially parallel with one another. The compliance members are also substantially parallel with one another and disposed on opposite sides of the spinal midline.

Figure 9D:
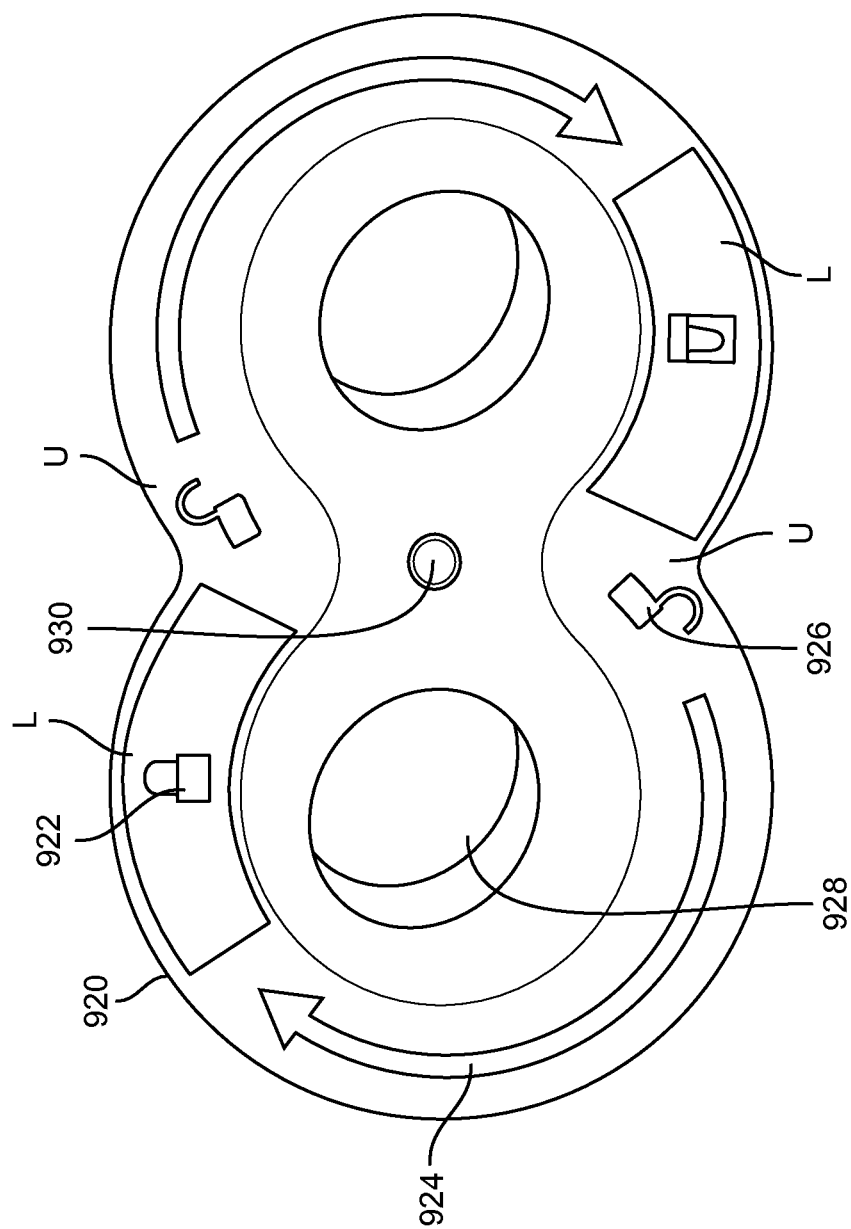

An indicator plate is shown in FIG. 9D that facilities actuation of the locking mechanisms. The indicator plate is generally a flat planar plate having at least one and preferably two through holes 928 for receiving the instruments for actuating the locking mechanism. The through holes 928 may be round or another shape sized to receive the instruments. In this embodiment, the holes are oblong in order to receive the actuating instruments and to allow them to move laterally within the hole in order to accommodate various anatomies such as spinal midline thickness. A central post 903 extends outward from the plate and serves as a stop to prevent overactuation of the locking mechanism as will be explained in greater detail below. The indicator plate also includes a first indicator 922 and a second indicator 926. The first indicator is preferably a lock symbol L which indicates when various parts of the locking mechanism are in a locked, tightened, or otherwise engaged position, and the second indicator 926 is preferably an unlocked symbol U which indicates when various parts of the locking mechanism are in an unlocked, loose, or otherwise disengaged position. An actuation indicator 924 also indicates the direction of actuation to actuate the locking mechanism from the unlocked to locked position. The indicator plate may be machined or molded from a polymer or a metal or other material, and the indicia may be printed thereon or laser etched into the plate.

Figure 9E:
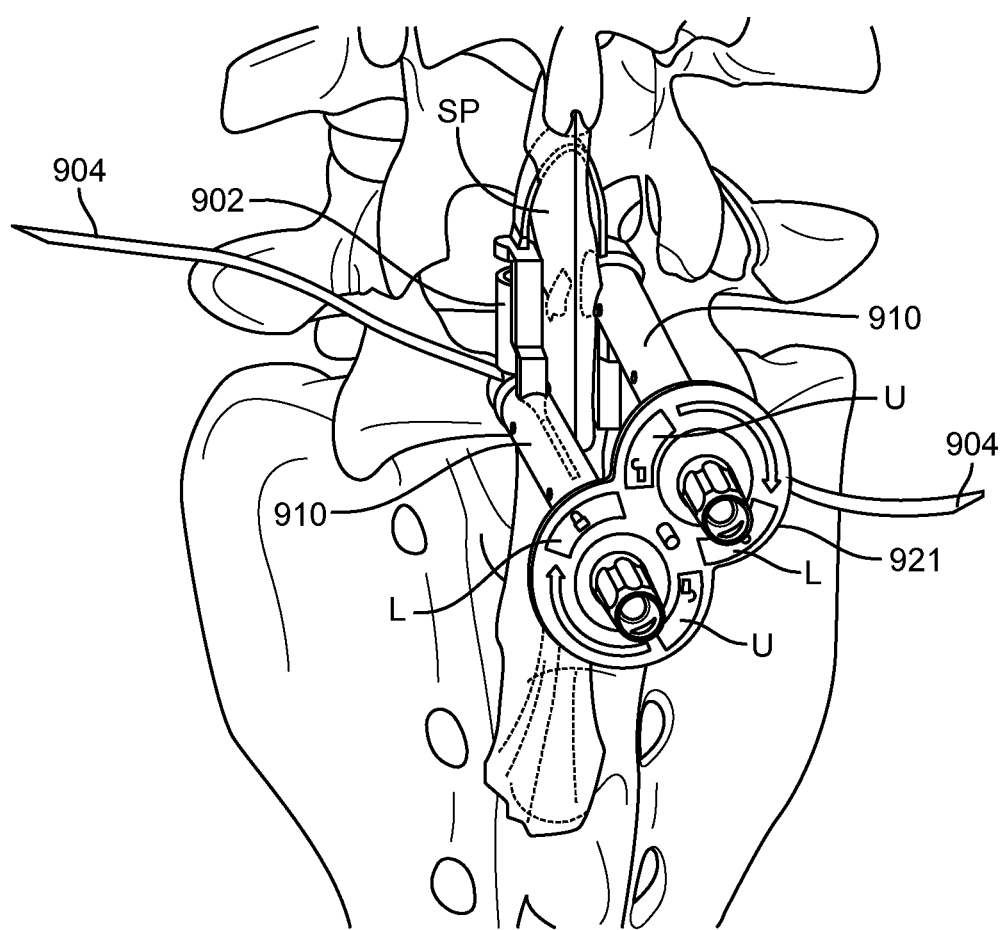
Figure 9F:
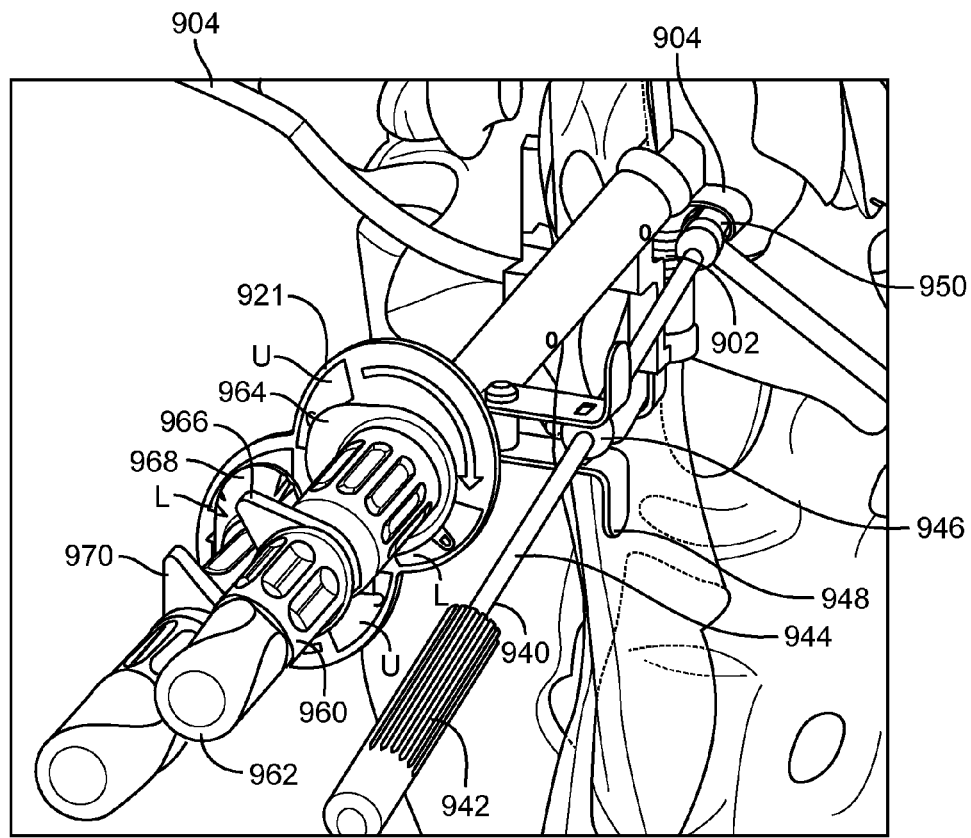

FIG. 9E illustrates the indicator plate 921 slidably disposed over both the elongate shafts of both holding instruments 910. This helps stabilize the instruments by constraining their movement. In FIG. 9F an inner driver 962, and an outer driver 906 are slidably disposed in the central channel of each of the holding instruments until their distal ends engage the locking mechanism in a compliance member 902. The inner driver 962 is also slidably disposed in the outer driver 960. Once the inner and outer drivers are engaged with the locking mechanism, a flag 964 (also referred to herein as a wing) on the outer driver and a flag 966 on the inner driver will be aligned with the unlocked symbol U on the indicator plate. One locking mechanism will be locked first by rotating the inner driver in a clockwise direction so that its flag 970 moves from the unlocked U to the locked position L. This actuates the roller which draws tether into the locking mechanism from two directions as described above, creating the friction fit which locks the tether in the locking mechanism. The outer driver is then actuated by rotating it clockwise so that its flag 968 moves from the unlocked U to the locked position L. This actuates the locking set screw (also referred to herein as a stopping element) and tightens it against the roller, thereby preventing the roller from moving or unwinding, thus the tether is locked into position. The outer driver may be referred to as a stopping instrument since it actuates the locking set screw, which stops or prevents actuation of the locking mechanism, the inner driver may be referred to as a locking instrument since it initially actuates the roller to lock the tether in place. In FIG. 9F the second locking mechanism on the second compliance member remains unlocked so that tether tension or loops size may be further adjusted. Additionally, a tightening tool 940 may be used to take up extra slack in the tether and tighten loop size or tension. The tightening tool 940 includes a handle 942 on the proximal end of an elongate shaft 944 and a slot 950 on the distal end is sized to receive the tether. Actuation of the tightening tool by rotating it either clockwise or counterclockwise spools the tether around the shaft 944 thereby reducing loop size and increasing tether tension, or by increasing loop size and decreasing tension. The tightening tool may also include a friction element 946 which is engaged by bracket 948 (also referred to as a braking clip or braking component) to hold tension in the tether after it has been tightened. The friction is sufficient enough to maintain the tension in the tether without requiring an operator to maintain torque on the shaft 944, thereby freeing up a surgeon's hand. Additionally, the friction is still low enough to be overcome when the inner driver tool is actuated drawing tether from both directions into the locking mechanism thus requiring that the tightening tool unwind slightly to allow the tether to be drawn into the locking mechanism. Additional details on this mechanism are described in greater detail below.

Figure 9G:
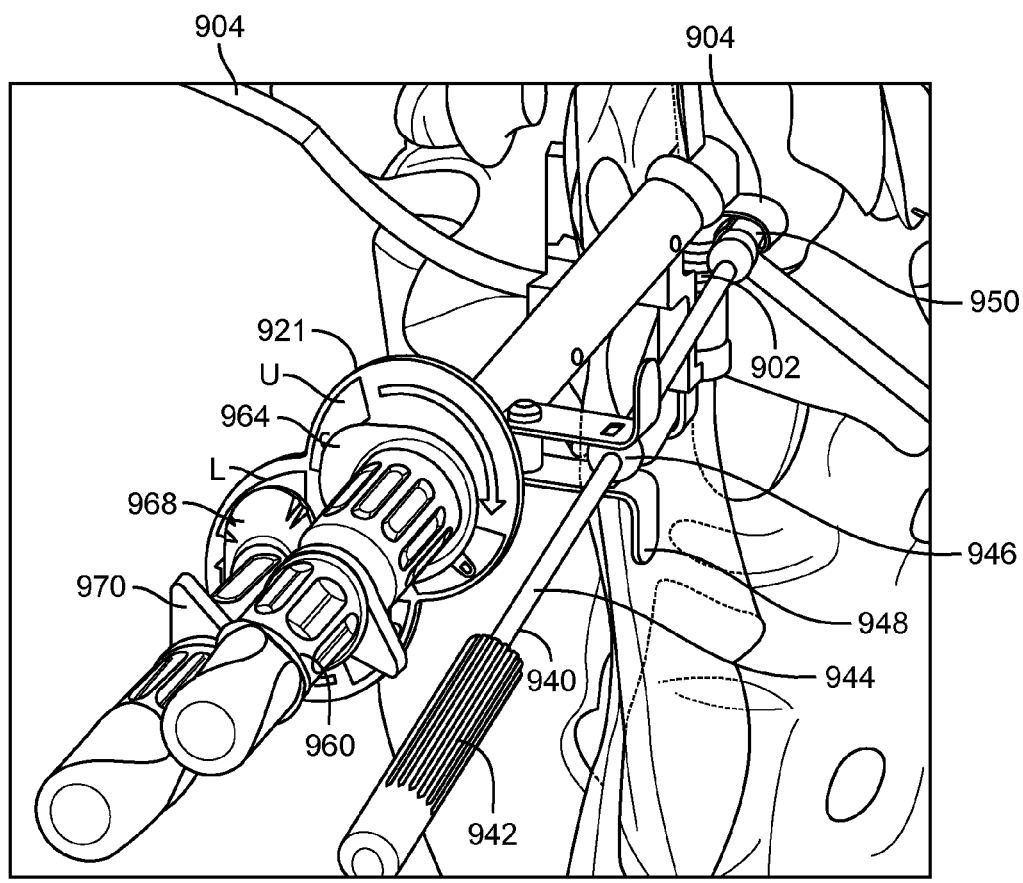
Figure 9H:
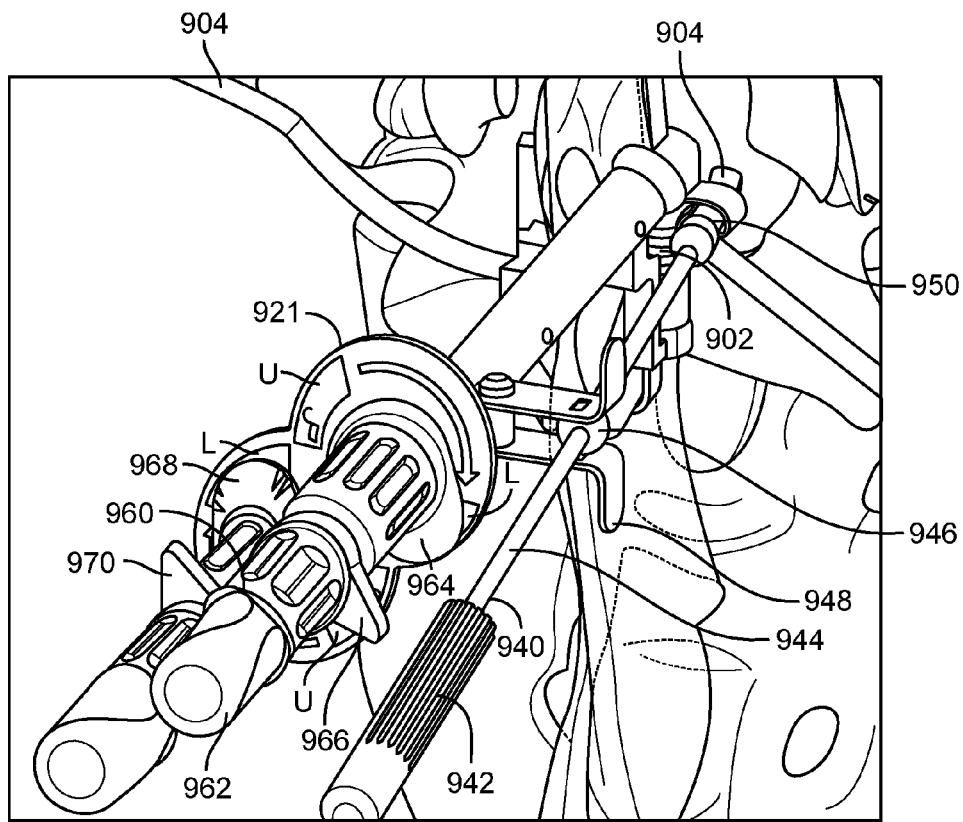
Figure 9I:
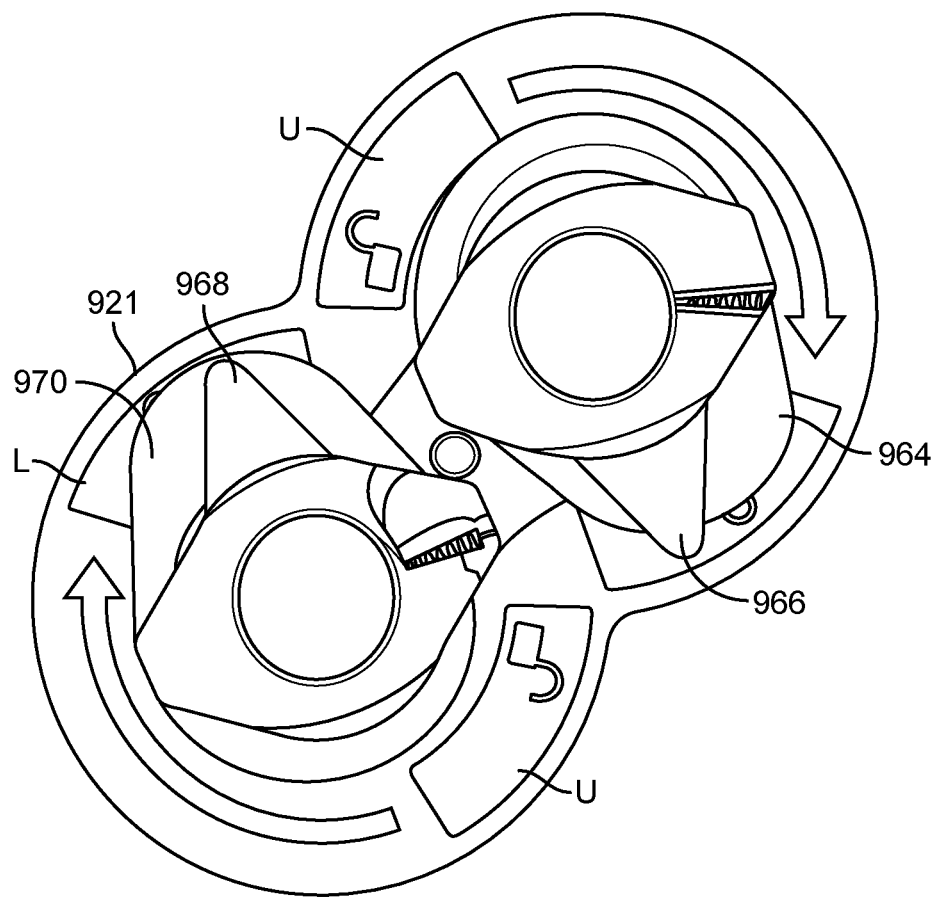

FIG. 9G illustrates actuation of the inner driver 962 by rotating it in a clockwise direction until flag 966 reaches the locked position L. In some embodiments, the inner driver cannot be over rotated because post 930 (best seen in FIG. 9D will interfere with flag 966 and prevent rotation therepast. Actuation of inner driver 962 draws the tether into the locking mechanism from both directions locking tether position. As previously mentioned, this also unwinds a portion of the tether from the tightening tool 940. In FIG. 9H the outer driver 960 is then actuated by rotating it in the clockwise direction until its flag 964 is disposed over the locked position L. Similarly, post 930 (best seen in FIG. 9D) prevents overactuation of the outer driver due to interference of the flag 964 with the post 930. Actuation of the outer driver threadably engages the locking set screw against the roller, thereby preventing further rotation of the roller. The tether is therefore locked in position and prevented from further movement by the set screw which acts as a stopping element or stopping mechanism. FIG. 9I illustrates both sets of inner and outer drivers now in the locked position. The tether is adjusted to the desired tension and/or loop size. The actuating instruments, indicator plate, and holding instruments may now be removed from the surgical field and excess tether severed. The procedure is completed with closure of the incision.

Tightening Instrument:

As previously discussed, when a tether tightening instrument is used to tighten the tether by spooling the tether around a shaft, the shaft must be held either manually or with another instrument so that tension is maintained while the locking mechanism is locked. Additionally, as the locking mechanism is actuated, the tether is drawn into the locking mechanism from two directions, thus as the tether is drawn into the locking mechanism, the tether must be slightly unspooled from the tightening instrument to ensure that the tether is properly tensioned. Thus, a surgeon must simultaneously actuate the locking mechanism with one hand while unspooling tether with another hand. Or, another instrument must be used to hold and release tension during various phases of tether adjustment. Thus, it would be advantageous to provide other tightening instruments which can free the surgeon's hands and hold or release tether tension as appropriate. FIGS. 10A-10E illustrate an exemplary embodiment of such a tightening instrument.

Figure 10A:
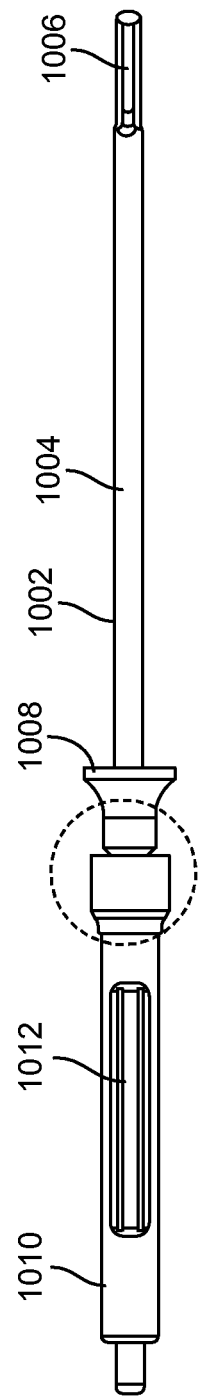
FIGS. 10A-10E illustrate an exemplary embodiment of a tightening instrument.
Figure 10B:
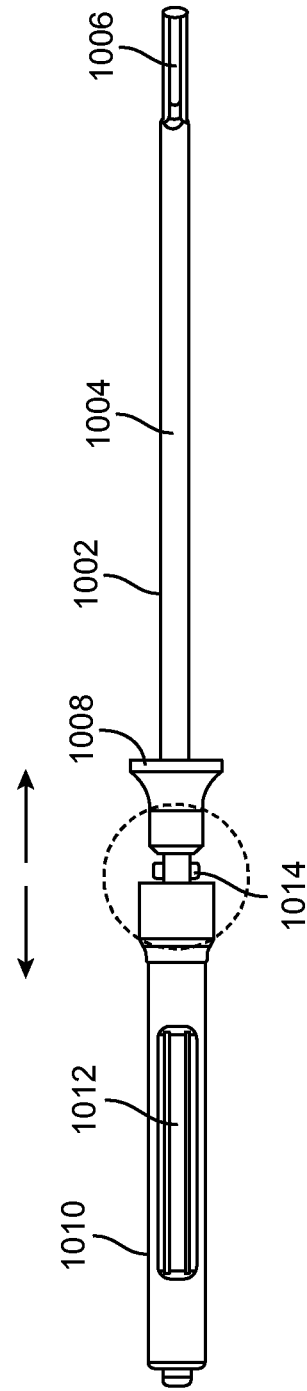

In FIG. 10A the tightening instrument 1002 includes an elongate shaft 1004 having a proximal end and a distal end. A slot 1006 is near the distal end and is sized to receive the tether such that rotation of the shaft will spool the tether around the shaft. A handle 1010 is coupled with the shaft 1004 by sliding the shaft into a central channel (not seen) in the handle. The shaft may have a friction fit with the handle, or in preferred embodiments the handle includes one or more friction tabs 1012 which frictionally engage the shaft. The handle is engageable and disengageable with the shaft as indicated by the arrows in FIG. 10A which shows the handle engaged with the shaft and FIG. 10B shows disengagement of the handle from the shaft. FIG. 10B also illustrates a cross pin 1014 which is used to help engage the handle with the shaft. Knob 1008 provides an area that is easy to grasp by the operator so that the handle may be engaged with and disengaged from the shaft. The cross pin may be press fit, bonded, welded, or otherwise attached to the shaft and is generally transverse to the longitudinal axis of the shaft.

Figure 10C:
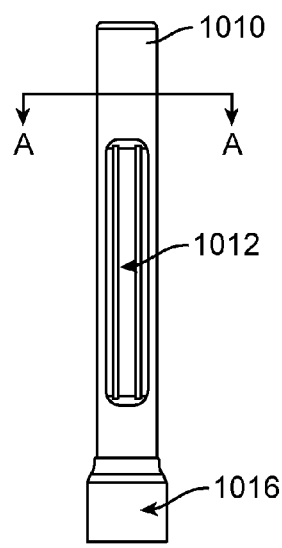
Figure 10D:
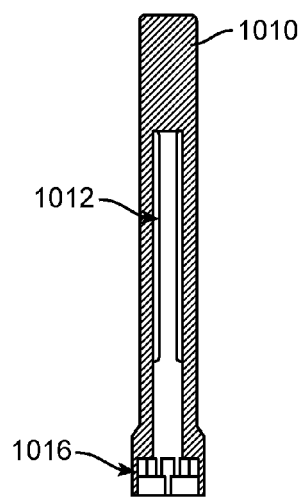
Figure 10E:
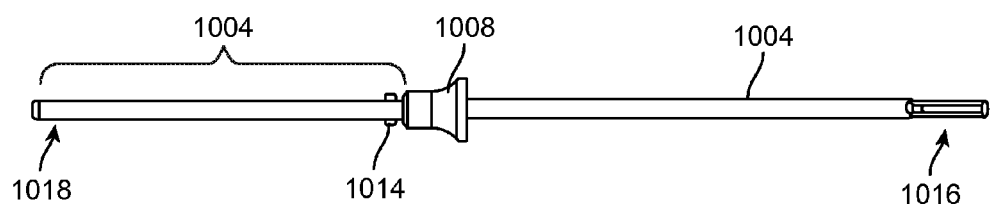

FIG. 10C more clearly illustrates the handle 1010 with friction tabs 1012 and a receptacle 1016 for the cross pin. FIG. 10D illustrates a cross-section taken along the line A-A in FIG. 10C and more clearly illustrates the receptacle for the cross-pin and the friction tabs 1012. FIG. 10E illustrates the elongate shaft more clearly including the slot 1016 for receiving the tether, the knob 1008, cross pin 1016, and a push pin 1018 for releasing the shaft from the handle.

In use, the embodiment of FIGS. 10A-10E is used first to spool the tether around the shaft thereby adjusting tether tension or tether loop size. This is accomplished by slidably engaging the handle with the shaft so that the cross pin is received in the handle receptacle. Once engaged, rotation of the handle is then transmitted to the shaft resulting in spooling or unspooling of the tether. The handle may be rotated clockwise or counter clockwise to spool the tether. Once the tether has been tensioned to a desired amount, the handle is disengaged from the shaft by moving the handle so that the cross pin is released from the receptacle. Because of friction between the handle and the elongate shaft, the shaft is prevented from rotating and thus the tether tension will be maintained without requiring a surgeon to hold the shaft. Friction between the handle and shaft is enough to prevent release of the tether tension until the locking mechanism is actuated creating a counter torque which draws the tether back into the locking mechanism. This requires that the tether unspool from the tightening instrument as the tether is drawn into the locking mechanism, and this force is high enough to overcome the friction between the handle and shaft thereby allowing unspooling. Thus the tightening device has a braking system that maintains tether tension after tension or tether size has been set and releases tether tension during locking of the tether.

One-Way Driver:

As discussed above, an inner driver and an outer driver are used to actuate the locking mechanism and set screw. Preferably the locking mechanism is locked by rotating the inner driver in a clockwise direction and similarly the set screw is tightened by rotating the outer driver the clockwise direction. Counter clockwise rotation will loosen the locking mechanism or loosen the set screw. While these rotation directions are fairly standard, it nevertheless can cause confusion to an untrained operator. Additionally, in some situations, counterclockwise actuation at the wrong time during the procedure can result in binding of the tether locking mechanism. Therefore, it is desirable to provide one-way drivers that can actuate a mechanism. Preferred embodiments of a one-way driver are described below and they can be used to actuate the locking mechanism and set screw described above, or they may be used to actuate other components and mechanisms where one-way driving is desirable.

Figure 11A:
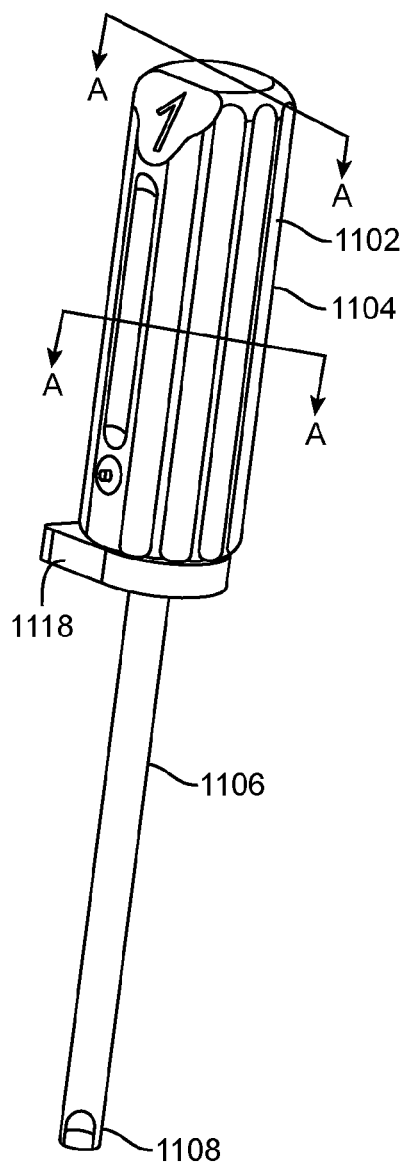
Figure 11B:
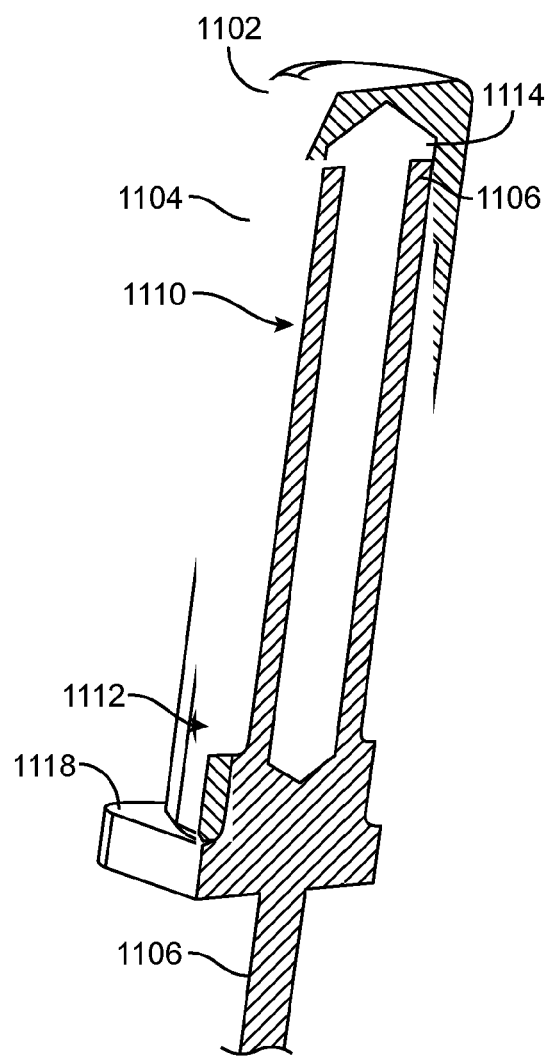

FIG. 11A illustrates an exemplary embodiment of a one-way driver 1102 having a handle 1104 and an elongate shaft 1106 coupled to the handle. The handle may be rotated in one-direction resulting in rotation of the shaft in the same direction. Rotation of the handle in the opposite direction uncouples the handle from the shaft such that the shaft does not rotate and thus the shaft will not rotate with the handle. A flag 1118 is coupled with the shaft 1106 so that as the shaft rotates, the flag 1118 will also rotate and this can help an operator keep track of the amount of rotation, especially when combined with an indicator plate such as previously described above. A distal engagement element 1108 may include various driver heads that can mate with any number of heads such as a flat head, Phillips head, Torx, hex, etc. FIG. 11B illustrates a cross-section taken along the line A-A in FIG. 11A and highlights the internal components of the one-way driver.

The handle 1104 includes a central channel 1114 for receiving a proximal portion of the elongate shaft 1106. A spring coil 1110 is disposed around the elongate shaft, and one end of the spring coil is formed so that a pin 1112 extends radially and laterally outward from the spring coil. The pin 1112 is then disposed in a hole 1116 in the handle (best seen in FIG. 11C) thus the coil spring is fixed to the handle. The opposite end of the spring coil may be fixed to the elongate shaft using methods known to those of skill in the art. Rotation of the handle in one direction will correspondingly rotate and tighten the coil spring against the shaft 1106 thereby resulting in rotation of the shaft. Rotation of the handle in the opposite direction will loosen the coil spring and disengage it from the shaft and thus the shaft will not rotate with the handle.

Figure 11F:
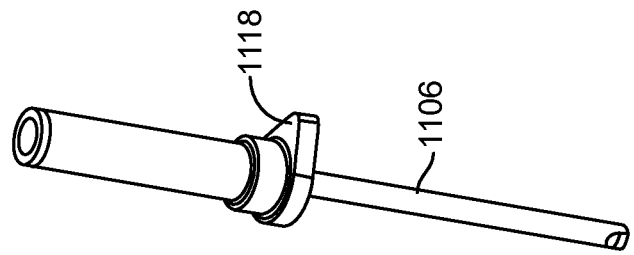
Figure 11E:
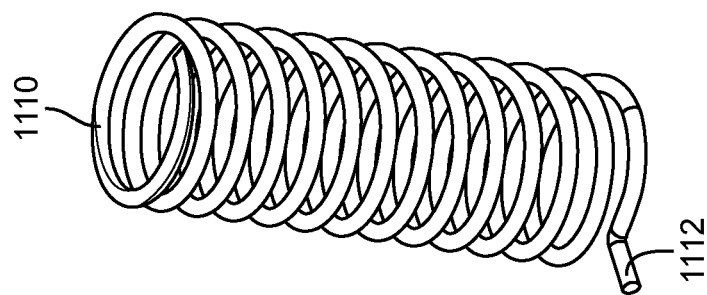
Figure 11D:
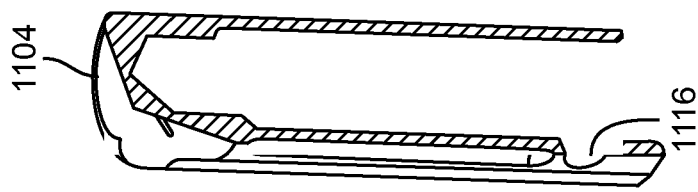
Figure 11C:
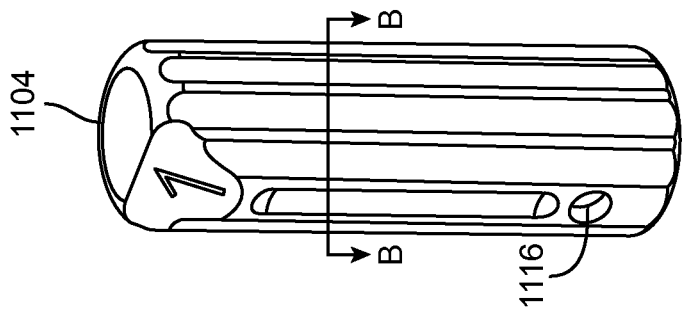

FIG. 11C illustrates the handle 1104 with hole 1116 for receiving the pin 1112, and FIG. 11D illustrates a cross-section taken along the line B-B in FIG. 11C. FIG. 11E illustrates the coil spring 1110 with pin 1112. The pin may be formed by bending a portion of the spring outward or by welding or otherwise joining the pin with the spring. FIG. 11F illustrates the shaft 1106 with indicator flag 1118. The proximal end of the shaft has a larger diameter section to provide a greater surface area over which the coil spring tighten and grasp the shaft. The material properties and geometry of the spring may be varied in order to provide desirable torque and other characteristics of the one-way driver.

Figure 11I:
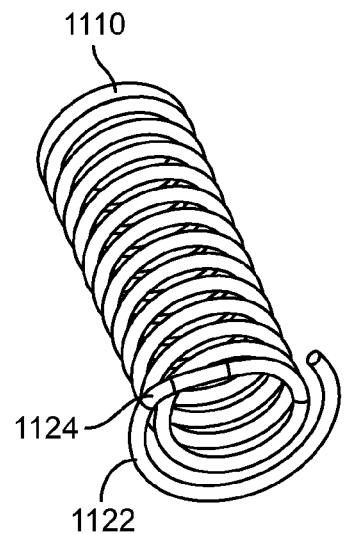
Figures 11J, 11K:
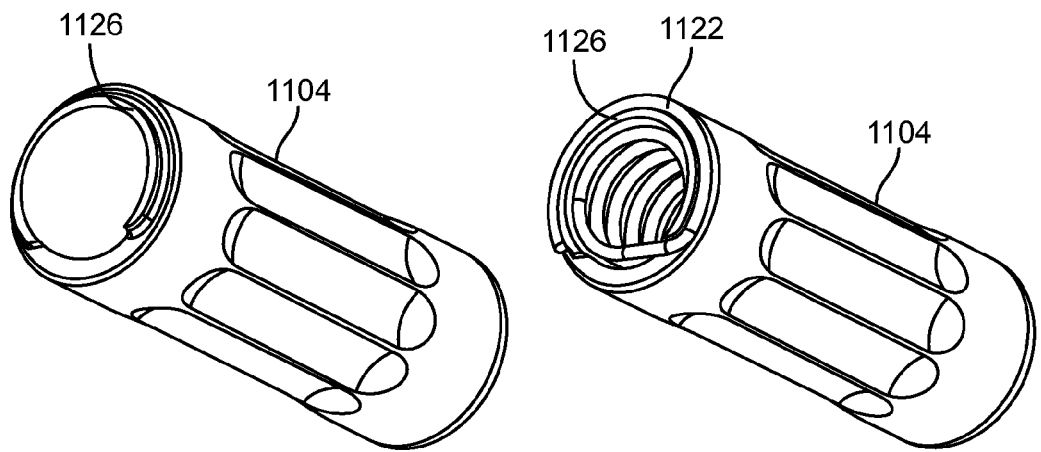

FIGS. 11G-11K illustrate an alternative embodiment of a one-way driver. FIG. 11G illustrates a handle 1104 having an end cap 1120 that is used to help secure the spring to the handle. FIG. 11H illustrates a cross-section of the handle taken along the line C-C in FIG. 11G in order to illustrate the internal components of the one-way driver. Similar to the previous embodiment, a coil spring 1110 is disposed on the handle and rotation of the handle increases or decreases the spring diameter so as to engage and disengage the shaft. An end portion of the coil spring has an enlarged diameter forming a flange 1122 that can be captured between the handle and the end cap. This couples the handle and spring so that rotation of the handle tightens and loosens the spring around the shaft. FIG. 11I illustrates the spring 1110 more clearly including the enlarged diameter flange section 1122 which may be formed integrally from the coil spring or a separate section may be attached to the coil spring at an attachment region 1124 which may be a welded region, adhesive region, threaded region, press fit region, or other coupling means may be used to join the flange with the spring. FIG. 11J illustrates a perspective view of an end of the handle which includes a rim 1126 that helps capture the flange on the spring as seen in FIG. 11K where the coil spring fits in a central channel of the handle and the flange rests against a distal end of the handle and also rests against the rim. The end cap 1120 is then threadably engaged, press fit or otherwise attached to the end of the handle thereby capturing the flange and operably coupling the spring with the handle. Operation of this embodiment is similar to the embodiment described above. Rotation of the handle in one direction tightens the spring onto the shaft so that the shaft will rotate with the handle, and rotation of the handle in the opposite direction loosens the spring and uncouples it from the shaft so that the shaft no longer rotates with the handle.

Braking Component:

Another exemplary embodiment that may be used to tighten the tether and hold tension without requiring an extra set of hands is illustrated in FIGS. 12-14C. This embodiment also will allow tension to be automatically released as the locking mechanism is actuated when the tether is drawn into the locking mechanism from two directions which requires unspooling of the tether from the tightening device.

FIG. 12 illustrates a tightening instrument 1202 which includes an elongate shaft 1204 having a handle 1210 on the proximal end of the shaft and a slot 1206 near the distal end of the shaft. The handle may include texturing 1212 such as knurling, channels, or other surface features which facilitate grasping by a surgeon. The slot 1206 is sized to receive the tether such that when the tightening instrument is rotated, the tether will spool around the shaft. A friction element 1208, here a spherical ball is disposed on the shaft and provides a location for coupling the tightening instrument with a braking component described below. The size of the friction element, as well as its surface finish may be adjusted in order to provide the desired amount of friction. When the tightening instrument is rotated and the tether is spooled around the shaft, the friction element engages the braking component with enough friction to prevent the tightening instrument from rotating and unspooling the tether. Similarly, when the locking mechanism is actuated which results in tether being drawn into the locking mechanism, the friction element engages the braking component with enough friction such that as the tether is drawn into the locking mechanism, the tether will unspool from the elongate shaft.

FIGS. 13A-13C illustrate an exemplary embodiment of a braking component that can be used with the tightening instrument in FIG. 12. The braking component includes a pair of straight or parallel arms 1302 that are coupled together with a rivet, screw, or other fastener 1310. One end of the arms is bent laterally outward to form an L-shaped leg 1304. The L-shaped legs provide a portion of the braking component that can easily grasped by a surgeon so that the component can be manipulated. For example, a surgeon may hold onto the legs and press the component into engagement with a tightening instrument or a holder instrument as will be described in greater detail below. The opposite end of the arms includes an arcuate or concave portion which allows that end to easily snap onto a cylindrical shaft. Holes 1306 near the L-shaped legs are sized to receive the friction element 1208 of the tightening instrument. FIG. 13A is a perspective view of the braking component, while FIG. 13B is a side view, and FIG. 13C is a top view of the component.

FIGS. 14A-14C illustrate how the braking component is used with the tightening tool. FIG. 14A illustrates a perspective view of the braking component 1301 engaged with the tightening instrument 1202 and a holding instrument 910 such as the one described previously. A tether and compliance member with locking mechanism 902 are coupled with the holding instrument 910. FIGS. 14B-14C are perspective views of the same thing but taken at different angles.

The compliance member and locking mechanism 902 are held in the cradle of the holding instrument 910. The concave portion 1308 of arms 1302 on component 1301 are snapped over the cylindrical shaft of the holding instrument 910. The snap fit is sufficient to prevent the component from sliding up and down the shaft or otherwise randomly disengaging therefrom. The tightening instrument is then snapped into the other end of the component such that friction element 1208 is positioned in holes 1306. In use, tightening instrument 1202 is rotated to spool the tether around the tightening instrument shaft. Once a desired tension is set, the operator may release the tightening tool and the friction between the component and the friction element will prevent unspooling of the tether from the shaft. When the tether is placed in the locking mechanism and the locking mechanism actuated, the tether will be drawn into the locking mechanism and this will automatically cause rotation and unspooling of the tether from the tightening instrument. The braking component is also advantageous since it helps hold the tightening instrument and the holding instrument upright, and prevents them from falling into the surgical field.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Additionally, while systems with various components are disclosed, one of skill in the art will also appreciate that in any of the embodiments disclosed herein, individual components or may be provided alone, or in combination or sub-combination with any of the other components. It is intended that the following claims define the scope of the invention and that methods and structures within the scope of these claims and their equivalents be covered thereby.

What is claimed is:

1. A system for adjusting tension in a surgical tether, said system comprising:

an implantable surgical tether structure having a tether comprising a free end and a locking mechanism adapted to receive the tether, the locking mechanism adapted to lock the free end of the tether in the locking mechanism when the tether is disposed in the locking mechanism such that the tether structure forms a loop that is adapted to encircle an anatomical structure, the locking mechanism adapted to allow adjustment of loop size or tension therein;

a locking instrument operably coupled with the locking mechanism, wherein actuation of the locking instrument in a locking direction frictionally locks the tether in the locking mechanism thereby preventing slidable movement of the tether;
a tightening instrument adapted to receive the free end of the tether, wherein actuation of the tightening instrument in a tightening direction reduces the loop size or increases loop tension, and wherein actuation of the tightening instrument in a loosening direction opposite the tightening direction increases the loop size or decreases loop tension; and
a braking component coupled to the tightening instrument, wherein the braking component is coupled to the tightening instrument with sufficient friction to hold the tightening instrument in a tightened position after actuation of the tightening instrument in the tightening direction, and
wherein the braking component is coupled to the tightening instrument with sufficient friction to allow the tightening instrument to move from the tightened position to a loosened position when the locking instrument is actuated in the locking direction, and
wherein the braking component comprises a first arm coupled to a second arm, the first and second arms adapted to flex outward and biased to return to an inward position, thereby frictionally coupling the braking component with the tightening instrument and
wherein the tightening instrument comprises a friction element, and wherein the first and second arms on an end of the braking component comprise an aperture for receiving the friction element.

2. The system of claim 1, wherein the surgical tether structure comprises a superior loop segment and an inferior loop segment, wherein the superior loop segment is adapted to be disposed around a superior spinous process, and the inferior loop segment is adapted to be disposed around an inferior spinous process or sacrum.

3. The system of claim 1, wherein the surgical tether structure comprises a first compliance member coupled with the locking mechanism, the first compliance member adapted to provide a force resistant to flexion of a spinal segment.

4. The system of claim 1, wherein the surgical tether structure further comprises a second compliance member disposed substantially parallel to the first compliance member, and wherein the first and second compliance members are adapted to be disposed on opposite sides of a spinal midline.

5. The system of claim 1, wherein the surgical tether structure further comprises a second locking mechanism adapted to receive the tether, the second locking mechanism adapted to lock the tether in the second locking mechanism when the tether is disposed therein, wherein the second locking mechanism is disposed substantially parallel to the other locking mechanism, and wherein the locking mechanisms are adapted to be disposed on opposite sides of a spinal midline.

6. The system of claim 1, wherein the locking mechanism comprises a roller rotatably disposed in a housing.

7. The system of claim 6, wherein the locking mechanism comprises a slot passing therethrough, the slot sized to receive the tether.

8. The system of claim 7, wherein the locking mechanism slot passes through the housing, and wherein the roller comprises a through slot, and wherein the slots are aligned with one another when the locking mechanism is unlocked.

9. The system of claim 6, wherein rotation of the roller into a locked position draws the tether into the housing from two directions.

10. The system of claim 6, further comprising a stop mechanism having an engaged position and an unengaged position, wherein in the engaged position the roller is prevented from rotating, and wherein in the unengaged position the roller is free to rotate.

11. The system of claim 1, wherein the locking instrument comprises an elongate shaft having a distal end adapted to be releasably coupled with the locking mechanism.

12. The system of claim 1, wherein the locking instrument comprises an inner shaft and an outer shaft, the inner shaft adapted to actuate the locking mechanism, and the outer shaft adapted to actuate a stop mechanism that prevents actuation of the locking mechanism into an unlocked position.

13. The system of claim 1, wherein actuation of the locking instrument in the locking direction draws the tether into the locking mechanism from two directions.

14. The system of claim 1, wherein the tightening instrument comprises an elongate shaft releasably coupled with the tether.

15. The system of claim 1, wherein the tightening instrument comprises a proximal end, a distal end, and a friction element disposed therebetween, the friction element adapted to allow the braking component to frictionally engage the tightening instrument.

16. The system of claim 15, wherein the friction element comprises a spheroid.

17. The system of claim 1, wherein the tightening instrument further comprises a handle coupled to a proximal end thereof.

18. A system for indicating status in a surgical tether locking mechanism, said system comprising:
an implantable surgical tether structure having a tether and a locking mechanism adapted to receive the tether, the locking mechanism adapted to lock the tether therein, the locking mechanism further comprising a stopping element adapted to prevent actuation of the locking mechanism;
a locking instrument operably coupled with the locking mechanism, wherein actuation of the locking instrument in a locking direction actuates the locking mechanism into a locked position wherein the tether is frictionally locked in the locking mechanism thereby preventing slidable movement of the tether;
a stopping instrument operably coupled with the stopping element, wherein actuation of the stopping instrument in an engaged direction actuates the stopping element into an engaged position which prevents actuation of the locking mechanism;
an indicator plate disposed adjacent the locking instrument and the stopping instrument, wherein the indicator plate has indicia that indicate when the stopping element is in the engaged position or a disengaged position, the indicia also indicating when the locking mechanism is in the locked position or in an unlocked position, the indicia further indicating actuation direction to actuate the stopping instrument between the disengaged and the engaged stopping element positions, or actuation direction to actuate the locking mechanism between the unlocked and locked positions; and
a post extending from the indicator plate, the post adapted to prevent over actuation of the stopping instrument beyond the engaged or disengaged stopping element positions, the post also adapted to prevent over actuation of the locking instrument beyond the locked and unlocked locking mechanism positions.

19. The system of claim 18, wherein the indicator plate comprises a through hole sized to slidably receive the stopping instrument and the locking instrument.

20. The system of claim 19, wherein the through hole is oblong thereby allowing lateral movement of the stopping instrument or the locking instrument when disposed therein.

21. The system of claim 18, wherein the indicator plate comprises a second through hole sized to slidably receive a second stopping instrument and a second locking instrument.

22. The system of claim 18, wherein the indicator plate comprises a figure eight shape.

23. The system of claim 18, wherein the indicator plate constrains lateral movement of the stopping instrument or the locking instrument.

24. A system for adjusting tension in a surgical tether, said system comprising:
an implantable surgical tether structure having a tether and a locking mechanism with a slot therein, the locking mechanism adapted to lock the tether when the tether is disposed in the slot; and
a tether tightening instrument adapted to tighten the tether, the tether tightening instrument comprising:
a handle having one or more friction elements, a central channel, and a receiver; and
an elongate shaft having a cross-pin and a slot near a distal end thereof sized to receive the tether,
wherein the elongate shaft further comprises a quick release knob for disengaging the elongate shaft from the handle, and
wherein the handle slidably receives the elongate shaft in the central channel, and
wherein rotation of the handle is transmitted into rotation of the elongate shaft when the cross-pin is engaged with the receiver so that the tether is tightened, and
wherein rotation of the elongate shaft is constrained due to friction between the elongate shaft and the one or more friction elements, but rotation of the elongate shaft is still permitted when sufficient counter torque is applied thereto, the constraint or rotation of the elongate shaft provided when the handle slidably receives the elongate shaft in the central channel and the cross-pin remains disengaged from the receiver so that the tether remains at least partially tightened.

25. The system of claim 24, wherein the one or more friction elements comprise tabs on the elongate shaft.

26. The system of claim 24, wherein the elongate shaft has a longitudinal axis and the cross-pin is transverse thereto.

27. The system of claim 24, wherein the slot slidably receives the tether and the tether is spooled around the elongate shaft when the elongate shaft is rotated in a first direction, and wherein the tether is unspooled from the elongate shaft when the elongate shaft is rotated in a second direction opposite the first direction.

* * * * *